(12) United States Patent
Gilmore et al.

(10) Patent No.: US 7,108,125 B2
(45) Date of Patent: Sep. 19, 2006

(54) EXTENDABLE BELT CONVEYOR

(75) Inventors: Phillip J. Gilmore, Healdsburg, CA (US); Shenghong Yang, Santa Rosa, CA (US)

(73) Assignee: Siemens Energy & Automation, Inc., Alpharetta, GA (US)

( * ) Notice: Subject to any disclaimer, the term of this patent is extended or adjusted under 35 U.S.C. 154(b) by 0 days.

(21) Appl. No.: 10/707,409

(22) Filed: Dec. 11, 2003

(65) Prior Publication Data

US 2004/0112719 A1    Jun. 17, 2004

Related U.S. Application Data

(60) Provisional application No. 60/319,783, filed on Dec. 13, 2002.

(51) Int. Cl.
*B65G 15/26* (2006.01)
*B65G 67/02* (2006.01)

(52) U.S. Cl. ............... 198/812; 198/594; 198/313; 414/398

(58) Field of Classification Search ............ 198/812, 198/594, 313; 414/398
See application file for complete search history.

(56) References Cited

U.S. PATENT DOCUMENTS

| | | | | |
|---|---|---|---|---|
| 2,558,629 A | 6/1951 | Smida | | 198/89 |
| 3,068,983 A | 12/1962 | McLaughlin | | 193/35 |
| 3,826,353 A | 7/1974 | Greasley | | 198/139 |
| 3,835,980 A | 9/1974 | Brooks, Jr. | | 198/139 |
| 3,935,941 A | 2/1976 | Keck | | 198/139 |
| 3,945,484 A * | 3/1976 | Oury | | 198/313 |
| 5,351,809 A | 10/1994 | Gilmore et al. | | 198/812 |
| 5,487,462 A * | 1/1996 | Gilmore | | 198/594 |
| 5,755,308 A | 5/1998 | Lindstrom et al. | | 186/66 |
| 6,006,893 A | 12/1999 | Gilmore et al. | | 198/588 |
| 6,431,346 B1 | 8/2002 | Gilmore et al. | | 198/588 |
| 6,481,563 B1 | 11/2002 | Gilmore et al. | | 198/511 |
| 6,481,566 B1 * | 11/2002 | Horak | | 198/812 |
| 6,484,862 B1 | 11/2002 | Gilmore et al. | | 193/35 TE |
| 6,533,096 B1 | 3/2003 | Gilmore et al. | | 193/35 TE |
| 2001/0009217 A1 | 7/2001 | Gilmore et al. | | 198/812 |

FOREIGN PATENT DOCUMENTS

| | | |
|---|---|---|
| DE | 2140708 | 2/1972 |
| GB | 2116940 A | 10/1983 |
| JP | 4277115 | 10/1992 |

OTHER PUBLICATIONS

International Search Report dated Apr. 2, 2004, from corresponding Patent Application Serial No. PCT/US03/39719.

* cited by examiner

*Primary Examiner*—Eileen D. Lillis
*Assistant Examiner*—Mark A. Deuble
(74) *Attorney, Agent, or Firm*—Van Dyke, Gardner, Linn & Burkhart, LLP

(57) ABSTRACT

An extendable conveyor includes a support structure, a mechanically extendable section which is extendable along the longitudinal axis between a fully retracted position and a fully extended position, a conveyor belt reeved among the mechanically extendable section thereby defining a conveying surface and a drive. The drive is operable to drive the conveyor belt in at least one direction. The extendable section may be extended by driving the conveyor belt in one direction and retracted by driving the conveyor belt in an opposition direction. The mechanically extendable section may include a plurality of sections at least one made substantially from a unitary sheet of material.

21 Claims, 20 Drawing Sheets

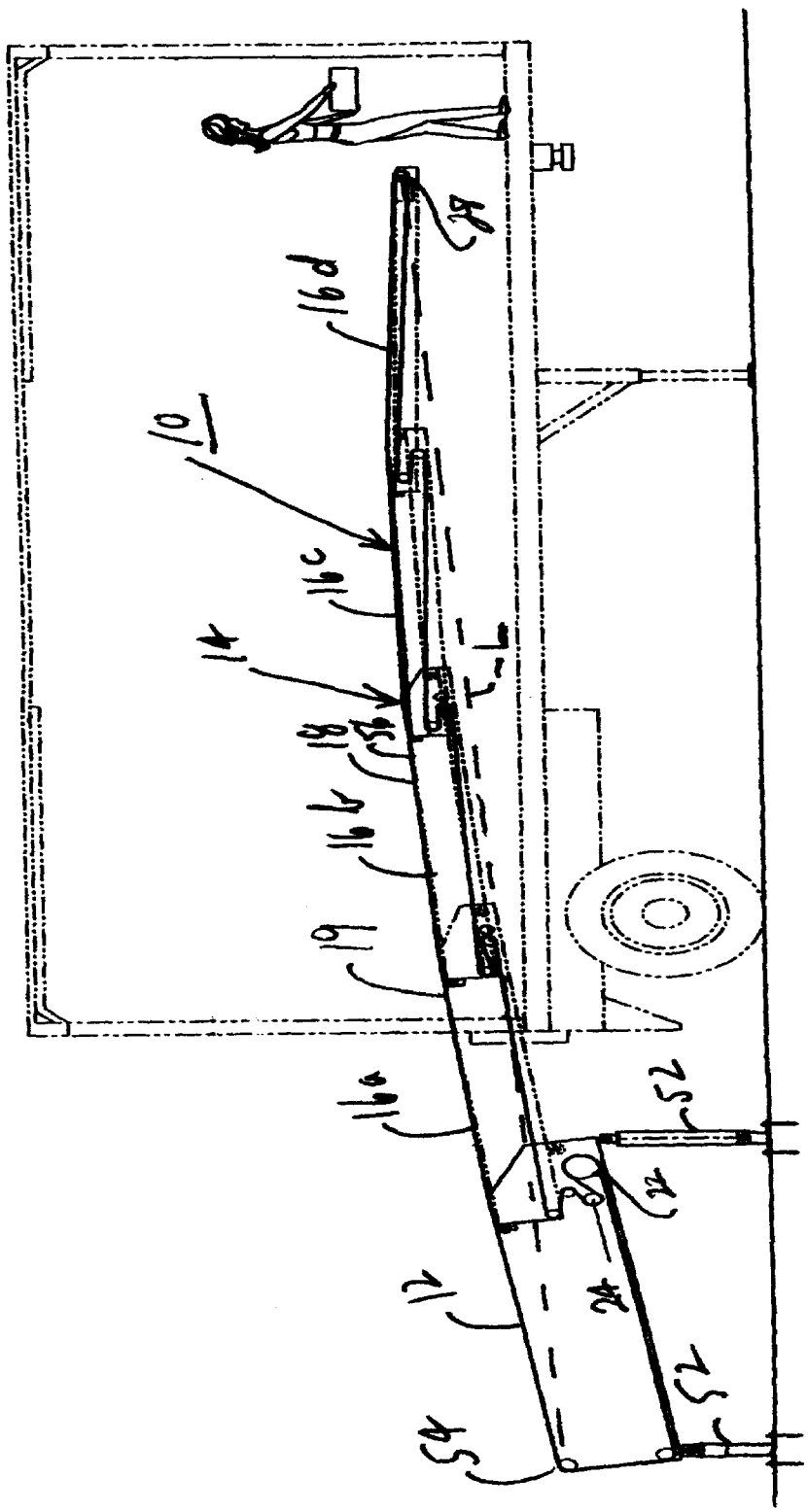

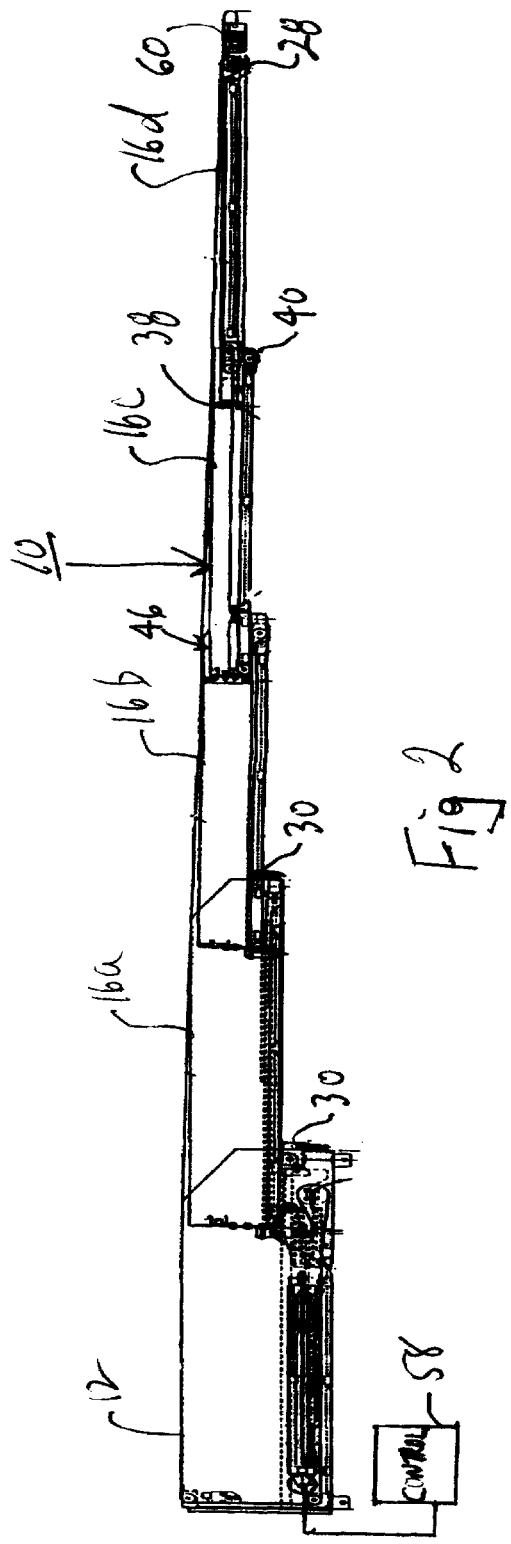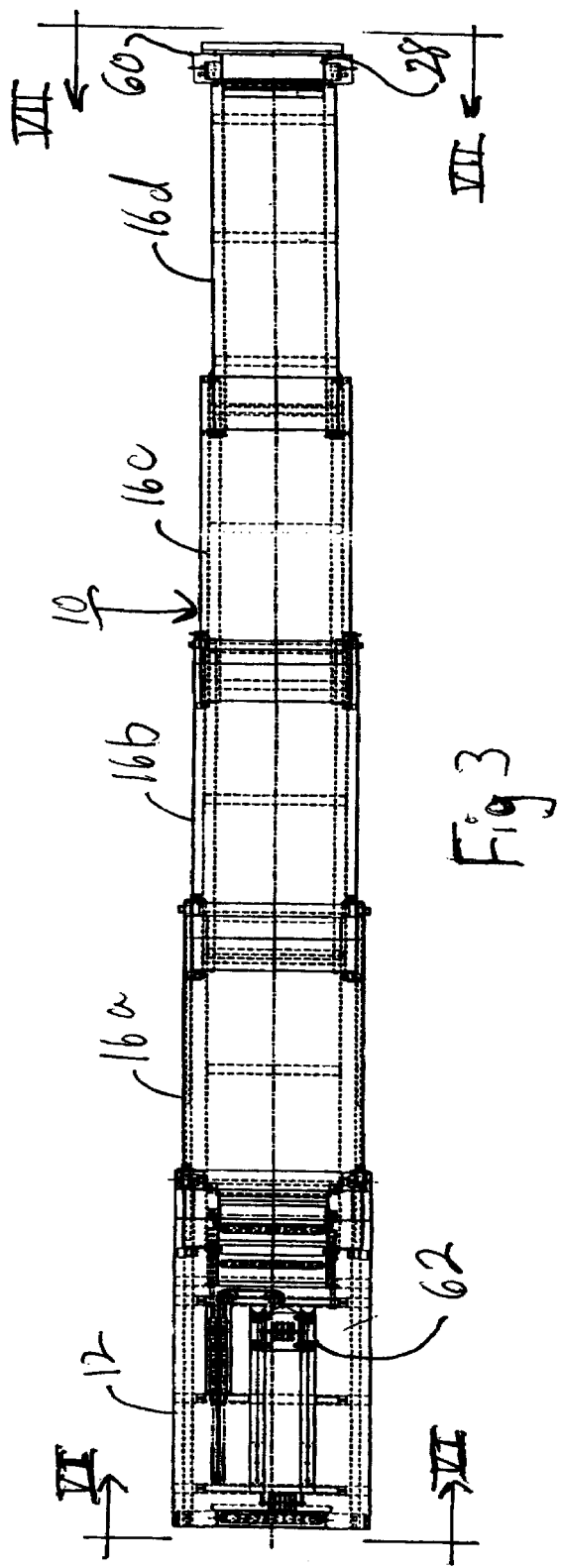

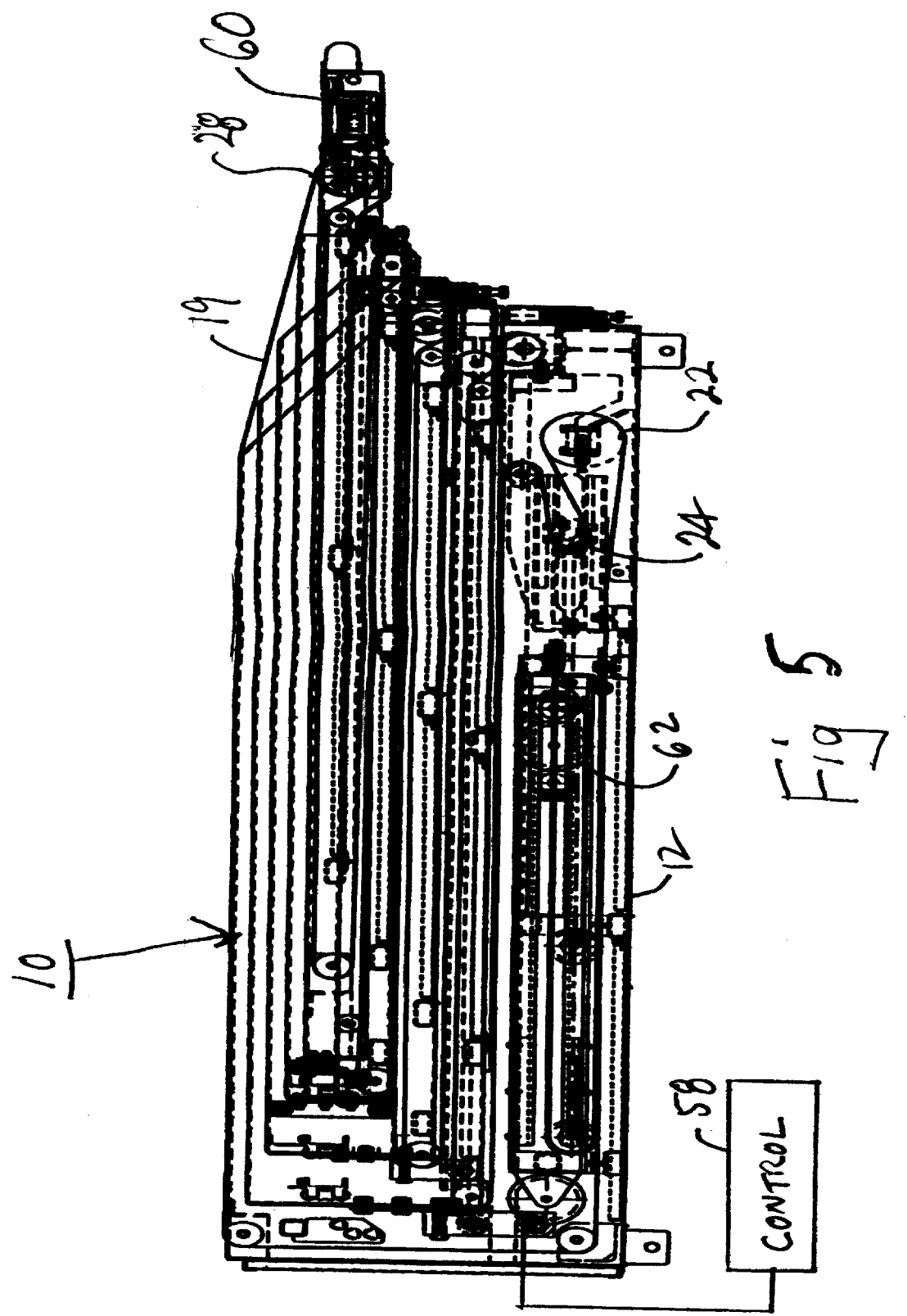

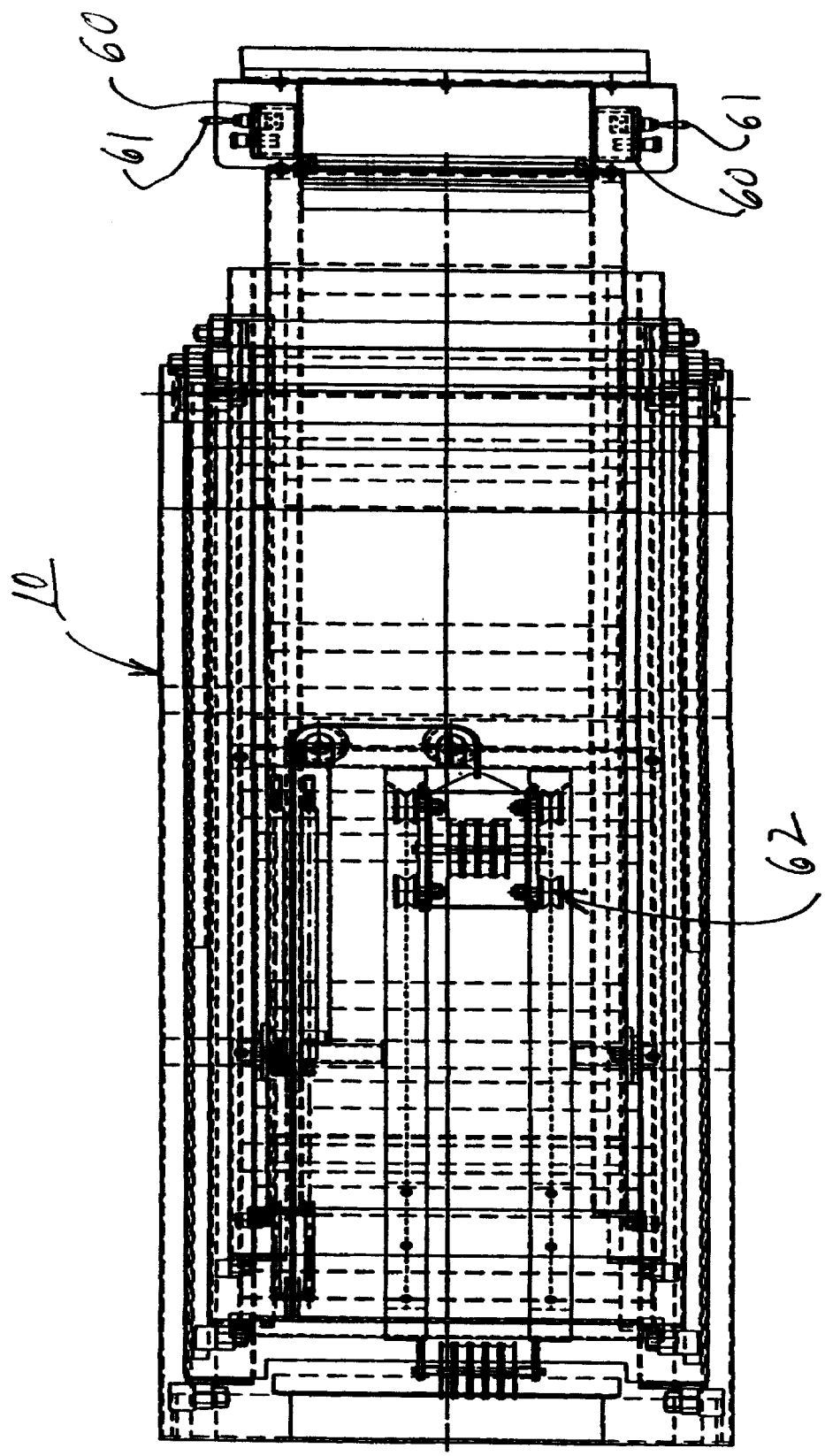

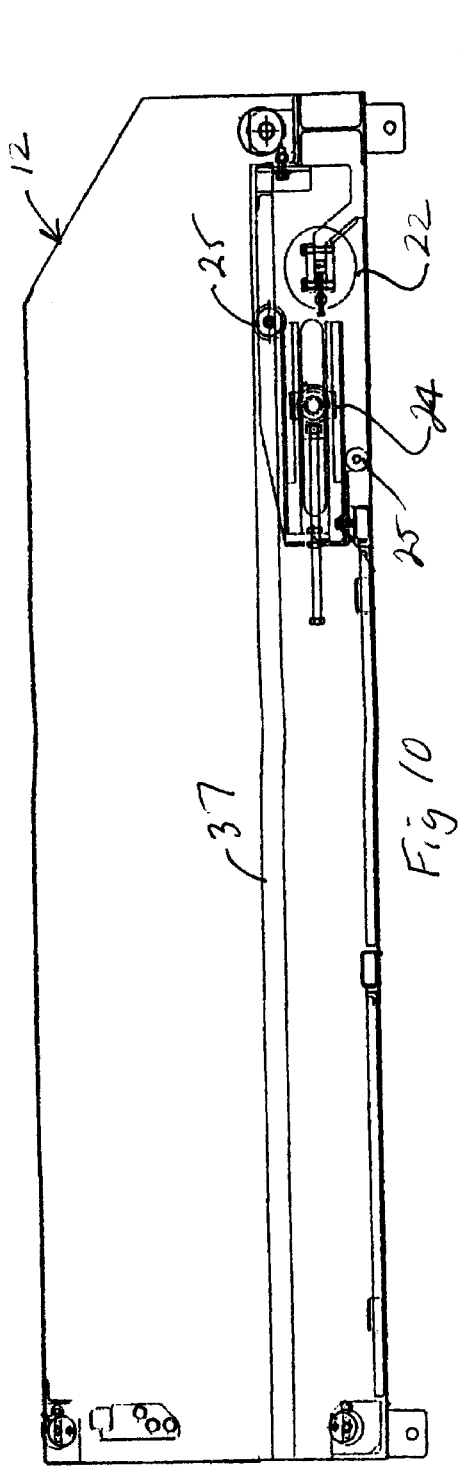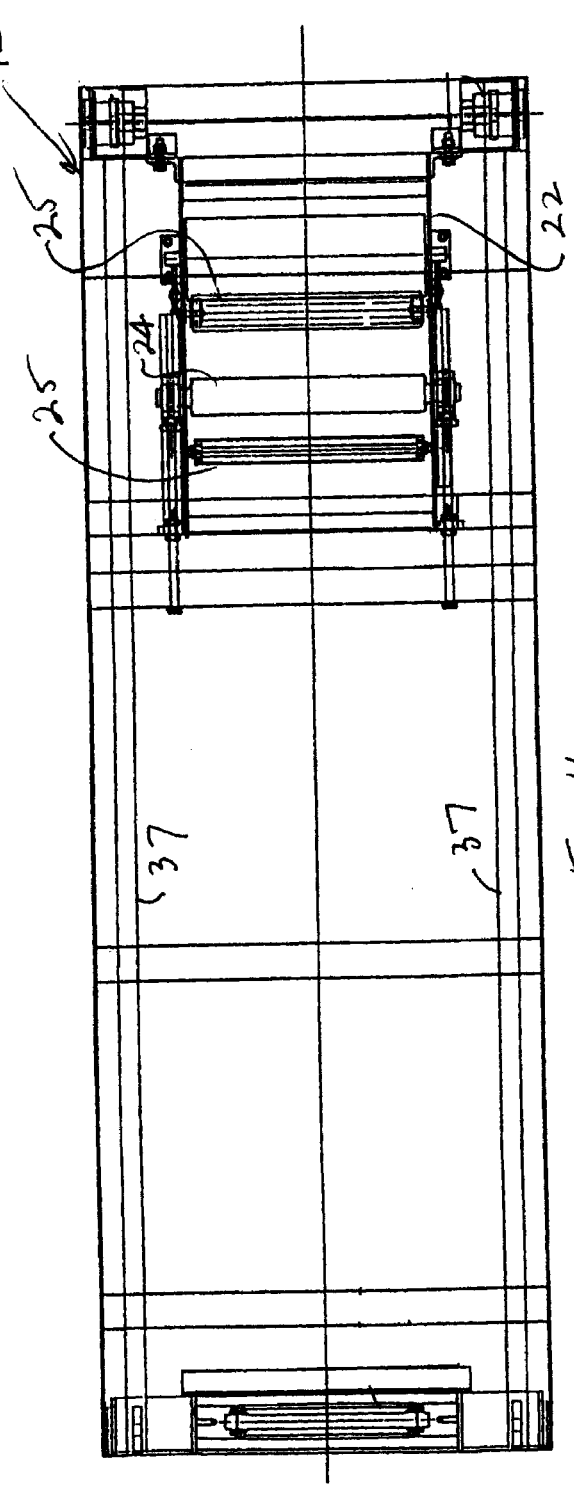

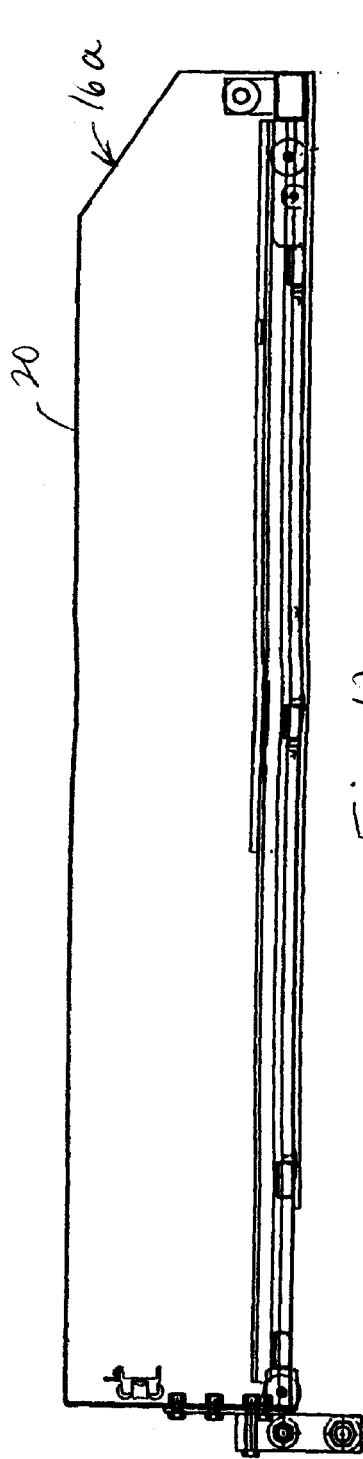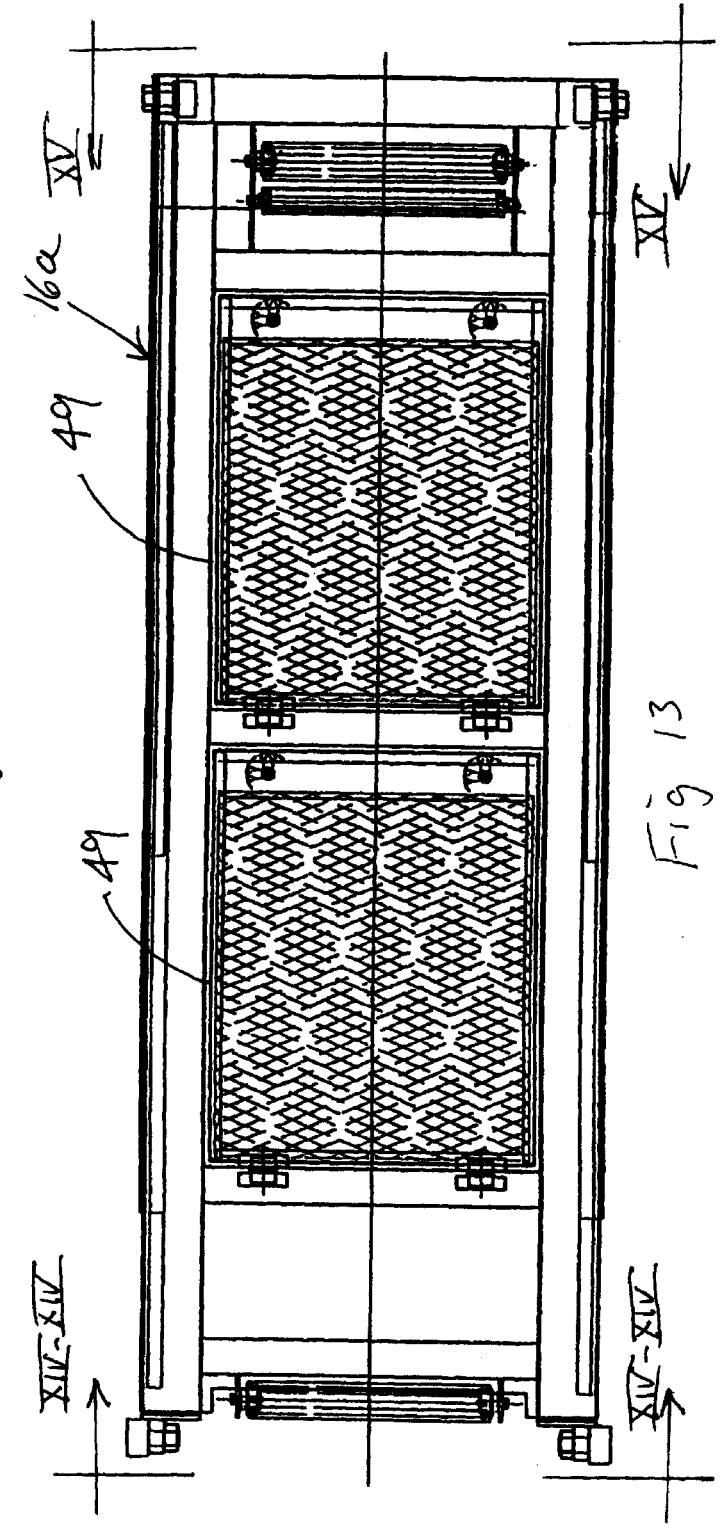

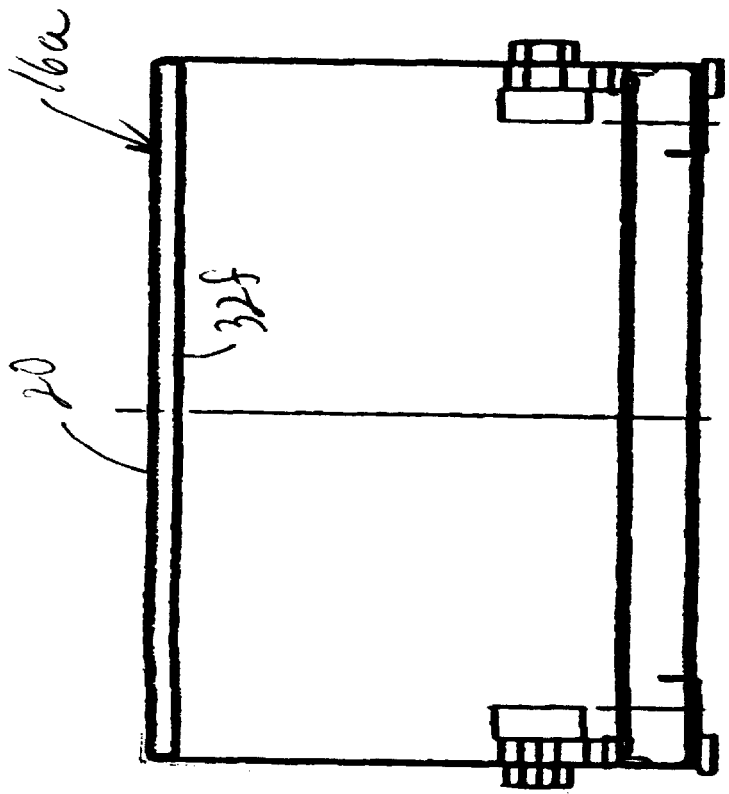
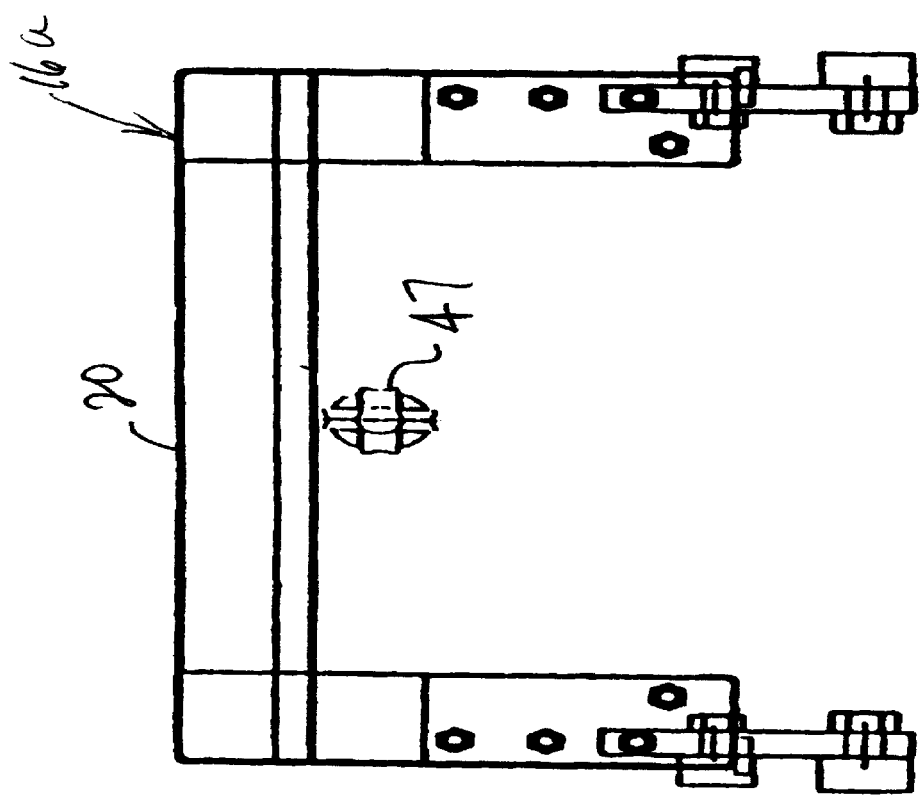

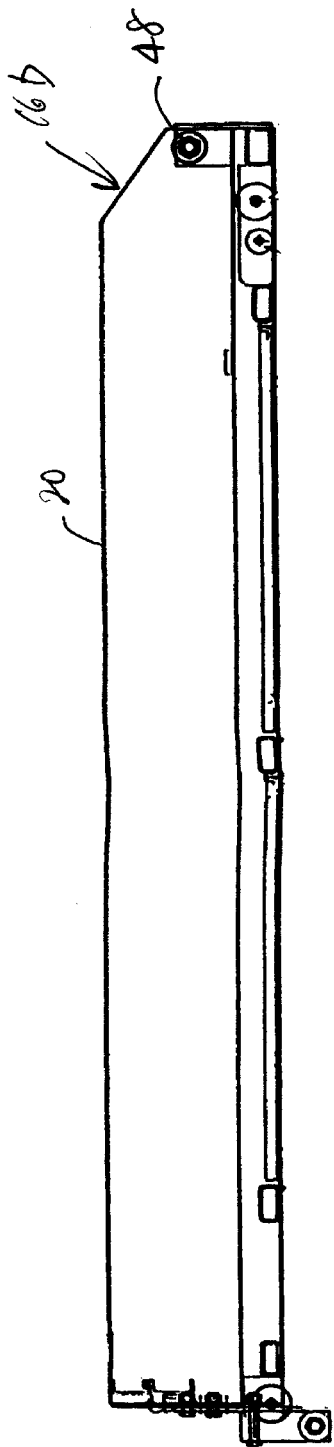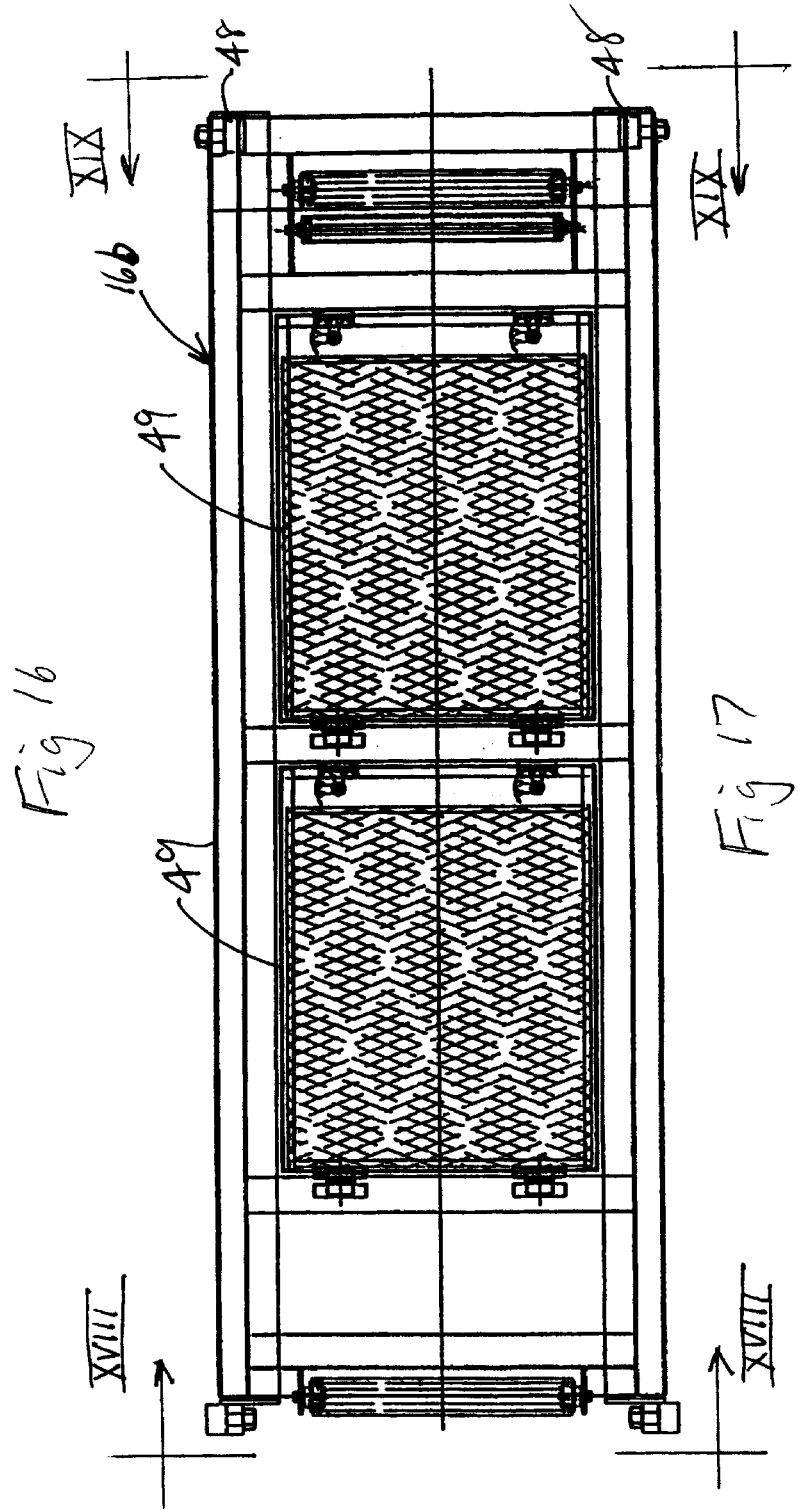
Fig 16
Fig 17

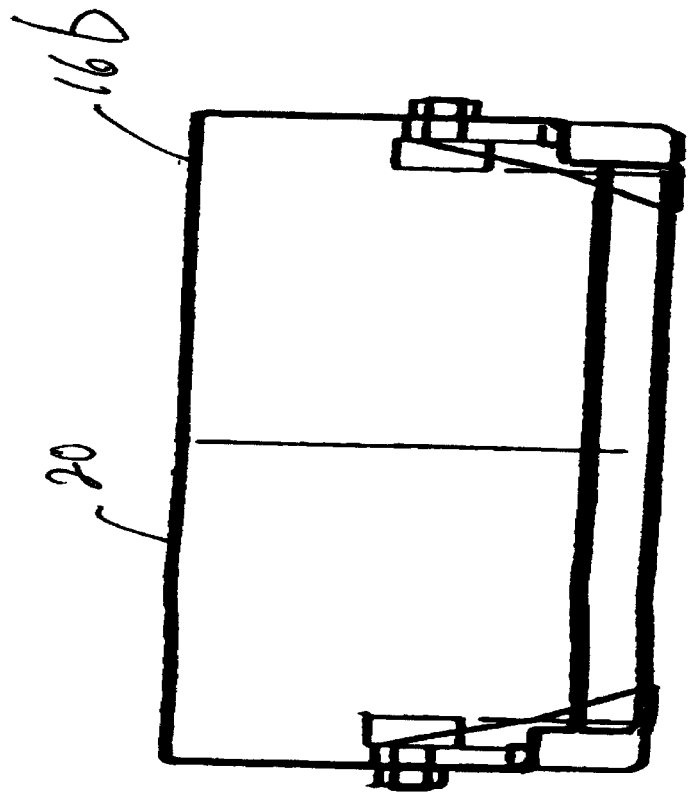
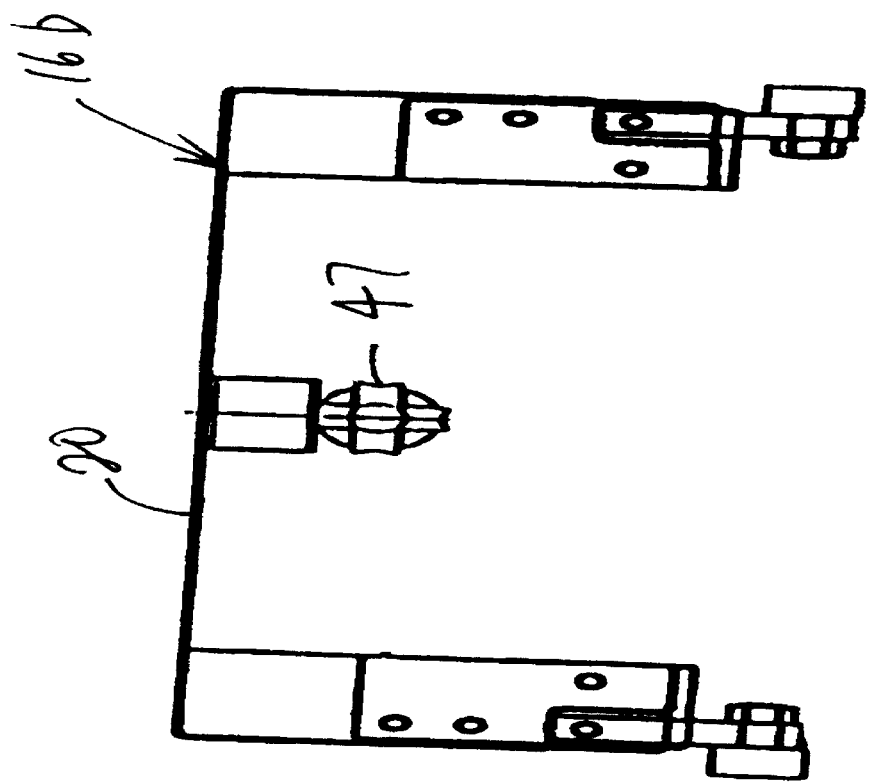
Fig. 19
Fig. 18

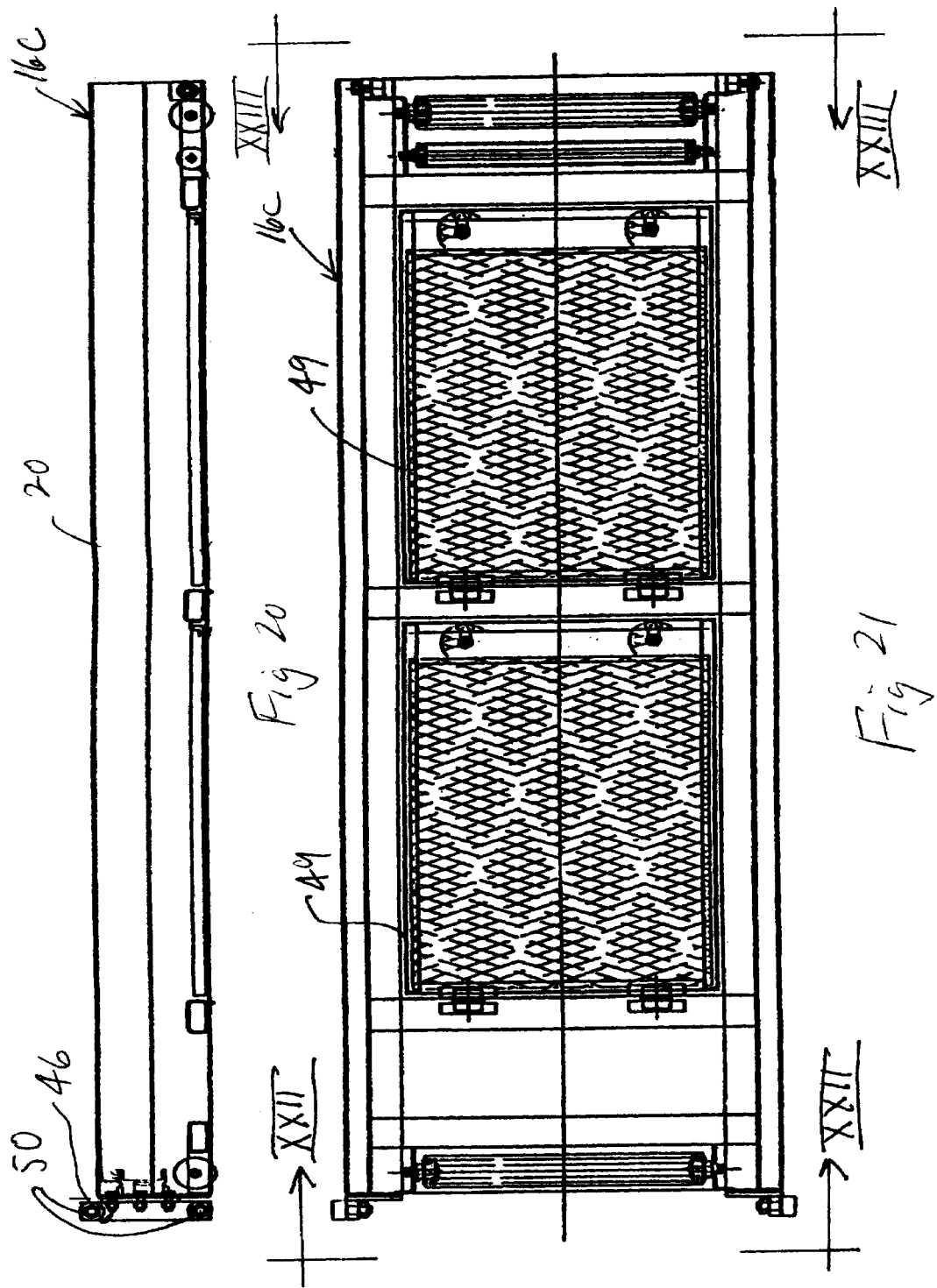

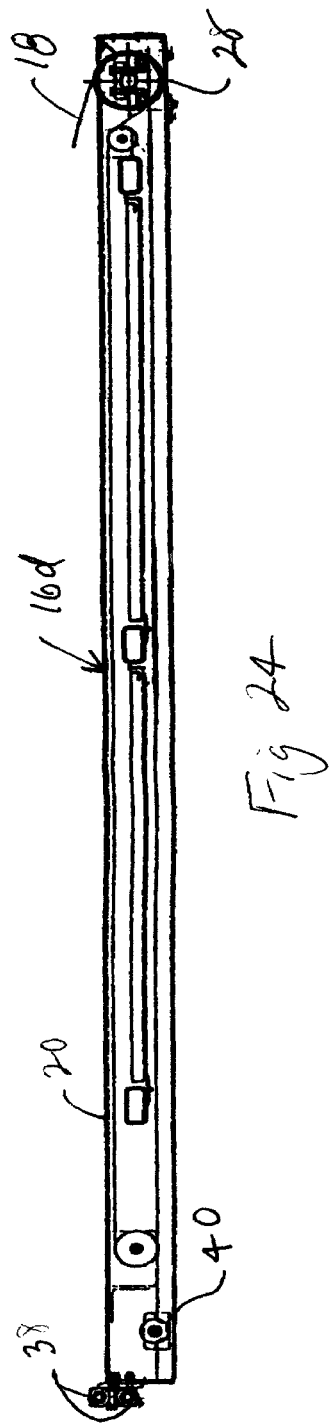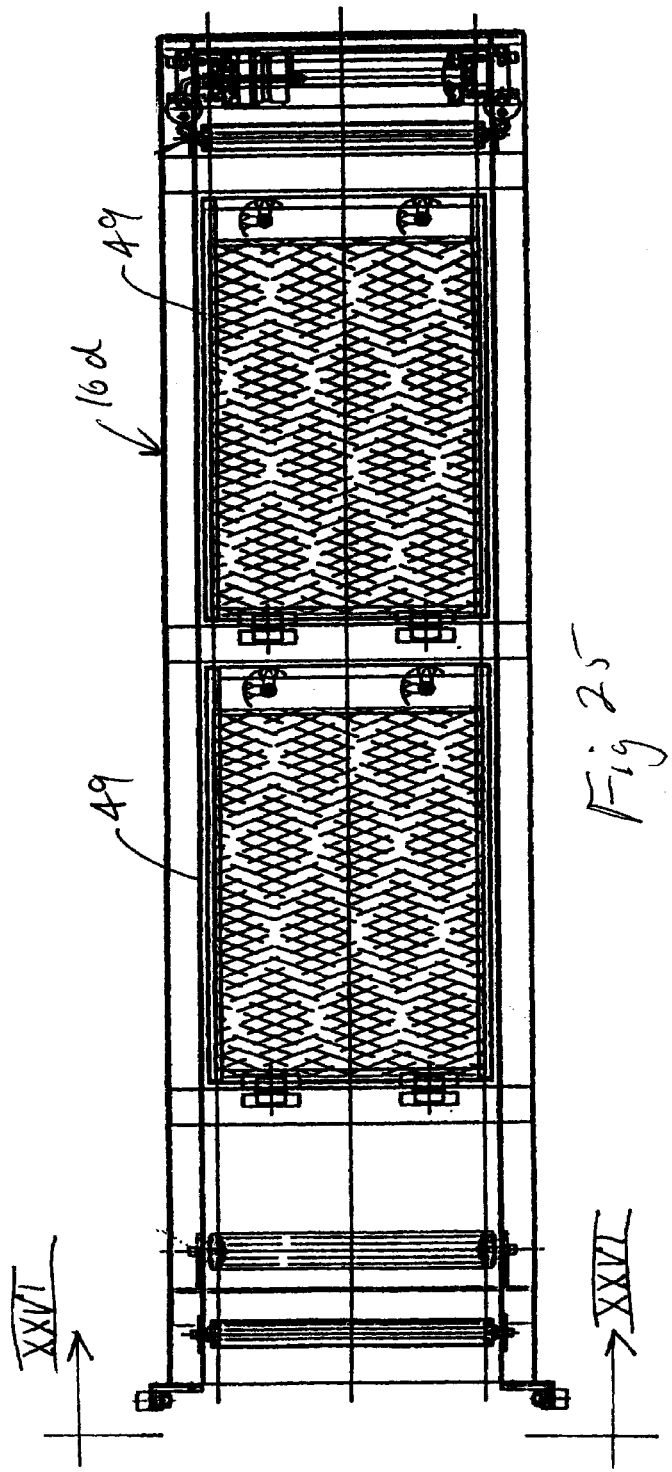

EXTENDABLE BELT CONVEYOR

CROSS REFERENCE TO RELATED APPLICATIONS

This application claims priority from U.S. provisional patent application Ser. No. 60/319,783, filed on Dec. 13, 2002, the disclosure of which is hereby incorporated herein by reference in its entirety.

BACKGROUND OF INVENTION

The present invention is directed to an extendable conveyor, such as a truck loader and/or unloader. While it may be useful with other types of extendable conveyors, the present invention is particularly useful in such a conveyor wherein the mechanically extendable section is supported in a cantilevered fashion by a support structure.

Extendable conveyors and, in particular, cantilevered supported extendable conveyors are known in the art. An example is disclosed in commonly assigned U.S. Pat. No. 5,351,809, the disclosure of which is hereby incorporated herein by reference. Because the extendable section is supported in a cantilevered fashion, it can be readily extended into, for example, a truck trailer in order to load and/or unload the trailer without regard for the condition of the floor of the trailer. One form of such an extendable conveyor has utilized a conveyor belt which is reeved with the booms of the extendable section in order to either supply articles to load the trailer or to withdraw articles to unload the trailer. In addition, a series of chains are utilized to either extend or retract the extendable section. Such an extendable conveyor as known in the '809 patent is fabricated from sheet metal members which are welded together in order to form the sections making up the mechanically extendable section.

While truck warehouses are often constructed with elevated docks, so that the floor of the trailer is at the same elevation as the warehouse floor, not all warehouses are constructed in this manner. This is especially true of small warehouses and warehouses located in city centers. In these types of warehouses, the floor of the warehouse is often at the level of the driveway supporting the truck trailer. This makes loading/unloading of the truck trailer more difficult. The warehouse end of the extendable conveyor is elevated so that the extendable section extends into the trailer at a proper operator height, which is deemed to be approximately waist high of the operator. Because the warehouse end needs to be elevated, the worker at the warehouse end must operate from an elevated platform and the conveyors servicing the extendable conveyor must also be elevated. Alternatively, in the case of a trailer unloader, a chute may be required in order to discharge the articles from the warehouse end of the extendable conveyor to the warehouse floor level.

SUMMARY OF INVENTION

The present invention provides an extendable belt conveyor which is capable of loading and/or unloading a truck trailer and which overcomes the deficiencies of the known extendable conveyors.

An extendable conveyor, according to an aspect of the invention, includes a support structure and an extendable section defined by at least one boom. The extendable section is incrementally extendable with respect to the support structure between a fully retracted position and a fully extended position. A conveyor belt is reeved among the support structure and the at least one boom of the extendable section thereby defining a conveying surface. A drive is operable to reversibly drive the conveyor belt in opposite directions. An electro-mechanical actuator is provided that is operative to impede movement of the belt with respect to the extendable section. A control is provided that at least partially extends the extendable section by controlling the drive to operate the conveyor belt in one direction and by controlling the electromechanical actuator to impede movement of the conveyor belt with respect to the extendable section. The control at least partially retracts the extendable section by controlling the drive to operate the conveyor belt in an opposite direction and by controlling the electromechanical actuator to impede movement of the conveyor belt with respect to the extendable section. The conveyor belt conveys articles by the control controlling the drive to operate the conveyor belt in one of the directions and by controlling the electromechanical actuator to not substantially impede movement of the conveyor belt with respect to the extendable section.

An extendable conveyor, according to another aspect of the invention, includes a support structure and an extendable section defined by at least one boom. The extendable section is incrementally extendable with respect to the support structure between a fully retracted position and a fully extended position. A drive is provided at the support structure and a braking pulley is provided at an outermost one of the at least one boom. The braking pulley is made up of a cylinder and a cylinder brake. The cylinder brake applies a braking force to the cylinder when actuated. A conveyor belt is reeved among the drive and the braking pulley, thereby defining a conveying surface. A control is provided that at least partially extends the extendable section by controlling the drive to operate the conveyor belt in one direction and by actuating the braking pulley. The control at least partially retracts the extendable section by controlling the brake to operate the conveyor belt in an opposite direction and by actuating the braking pulley. The conveyor belt conveys articles by the control controlling the drive to operate the conveyor belt in one of the directions and by the control deactuating the braking pulley.

An extendable conveyor, according to another aspect of the invention, includes a support structure and an extendable section defined by at least one boom. The extendable section is incrementally extendable with respect to the support structure between a fully retracted position and a fully extended position. A drive is provided at the support structure and a motorized pulley at an outermost one of the at least one boom. A conveyor belt is reeved among the drive and the motorized pulley thereby defining a conveying surface. The motorized pulley includes a cylinder and an electrical motor. The electrical motor rotates the cylinder when electrical energy is applied to the electrical motor. A control is provided that at least partially extends or retracts the extendable section controlling the drive to operate the conveyor belt and controlling the electrical motor at a speed less than the speed of the drive. The conveyor belt conveys articles by the control controlling the drive and the electrical motor at a common speed to operate the conveyor belt.

An extendable conveyor, according to another aspect of the invention, includes a support structure and an extendable section made up of a plurality of booms. The booms are extendable between a fully retracted position and a fully extended position. The extendable section is supported in a cantilevered fashion by the support structure. A conveyor belt is reeved among the booms, thereby defining a conveying surface. A drive is operable to drive the conveyor belt in at least one direction. At least one of the booms is made substantially from a unitary sheet of metal substantially forming a horizontal belt supporting surface and support sides extend from the belt supporting surface. The belt supporting surface supports a portion of the conveyor belt at the conveying surface.

An extendable conveyor, according to an additional aspect of the invention, includes a support structure and an extendable section made up of a plurality of booms. The booms are extended along a longitudinal axis between a fully retracted position and a fully extended position. The extendable section is supported in a cantilevered fashion by the support structure. A conveyor belt is reeved among the booms, thereby defining a conveying surface. A drive is operable to drive the conveyor belt in at least one direction. The extendable section is bowed when in an extended position, wherein a central portion of the conveying surface is above an imaginary straight line extending between opposite end portions of the conveying surface.

These and other objects, advantages and features of this invention will become apparent upon review of the following specification in conjunction with the drawings.

BRIEF DESCRIPTION OF DRAWINGS

FIG. 1 is a side elevation of an extendable conveyor illustrated in its intended environment;

FIG. 2 is the same view as FIG. 1 showing additional details of the extended conveyor in a fully extended position;

FIG. 3 is a top plan view of the extendable conveyor in FIG. 2;

FIG. 5 is a side elevation of the extendable conveyor in FIG. 2 in a fully retracted position;

FIG. 8 is a top plan view of the extendable conveyor in FIG. 1;

FIG. 10 is a side sectional view of the support structure;

FIG. 11 is a top plan view of the support structure in FIG. 10;

FIG. 12 is a side elevation of the first, innermost boom;

FIG. 13 is a bottom plan view of the boom in FIG. 12;

FIG. 14 is an end elevation taken from the direction XIV—XIV in FIG. 13;

FIG. 15 is an end elevation taken from the direction XV—XV in FIG. 13;

FIG. 16 is a side elevation of the second boom;

FIG. 17 is a bottom plan view of the boom in FIG. 16;

FIG. 18 is an end elevation taken from the direction XVIII—XVIII in FIG. 17;

FIG. 19 is an end elevation taken from the direction XIX—XIX in FIG. 17;

FIG. 20 is a side elevation of the third boom;

FIG. 21 is a bottom plan view of the boom in FIG. 20;

FIG. 24 is a side elevation of the fourth boom;

FIG. 25 is a bottom plan view of the boom in FIG. 24;

DESCRIPTION OF THE PREFERRED EMBODIMENT

Figure 4:
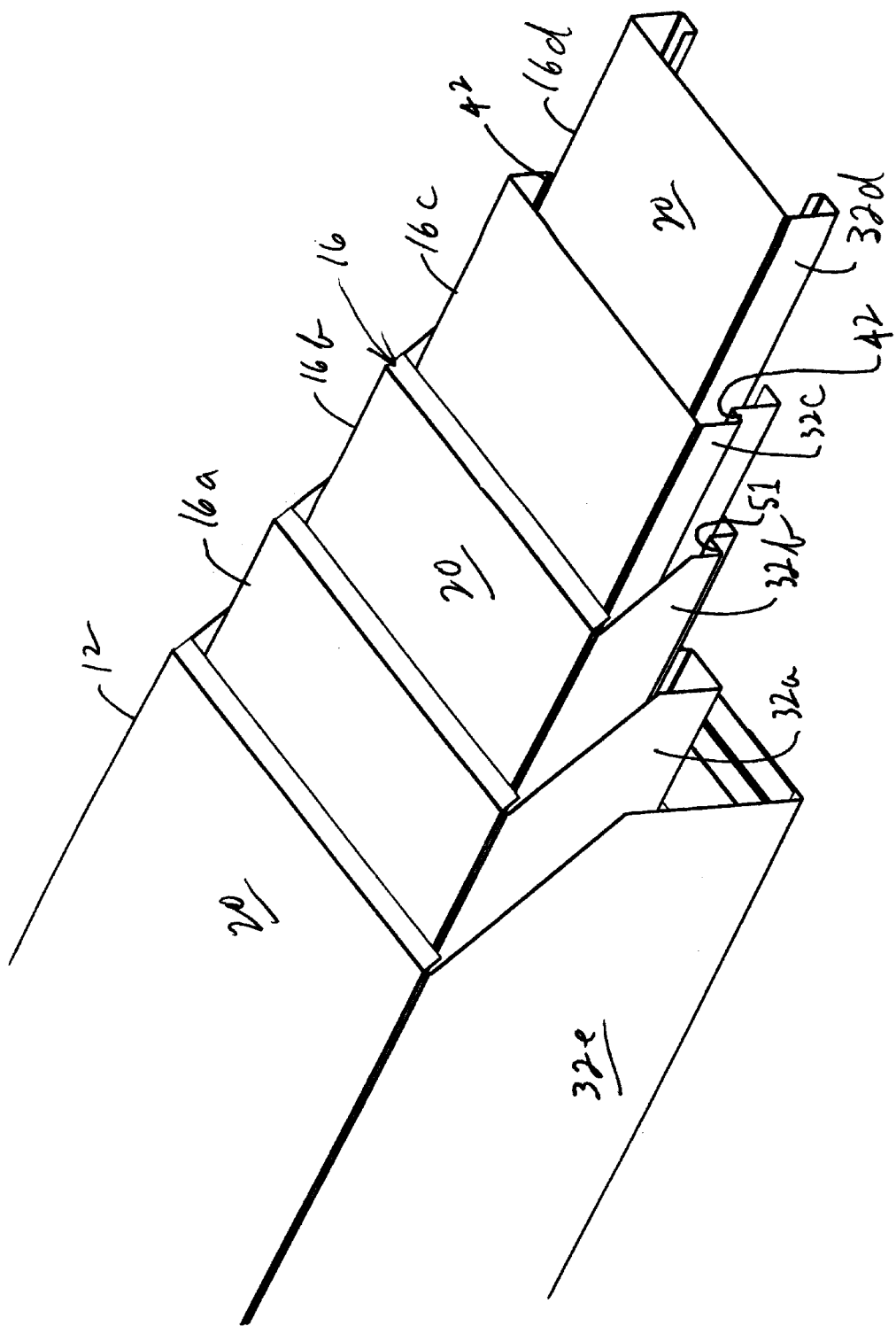
FIG. 4 is a perspective view of the booms making up the mechanically extendable section of the extendable conveyor.
Figure 7:
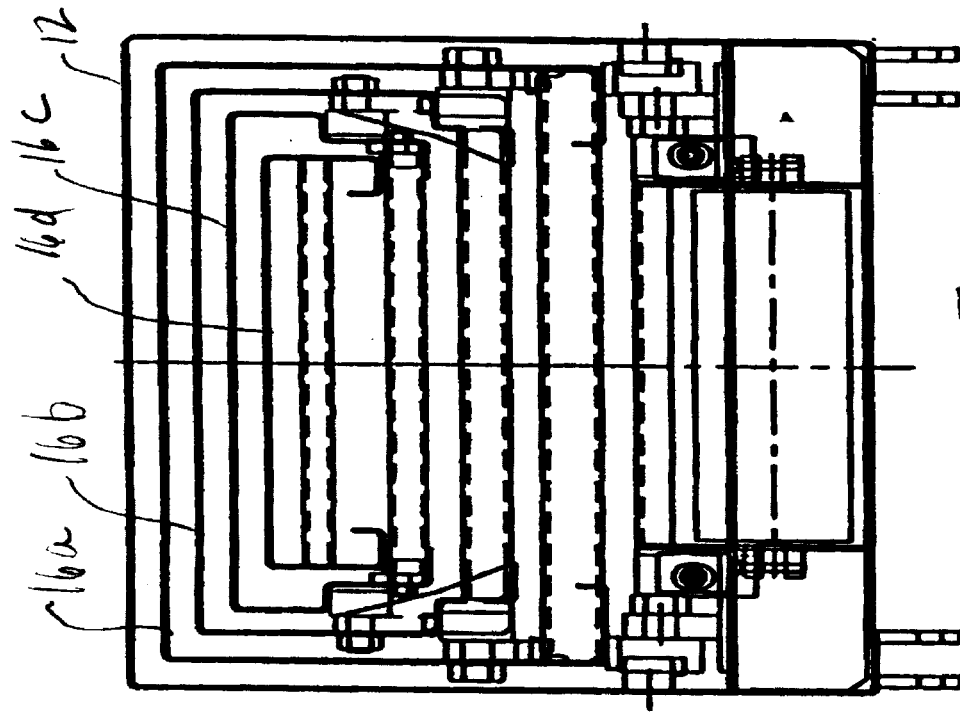
FIG. 7 is an opposite end elevation taken from the lines VII—VII in FIG. 3.
Figure 6:
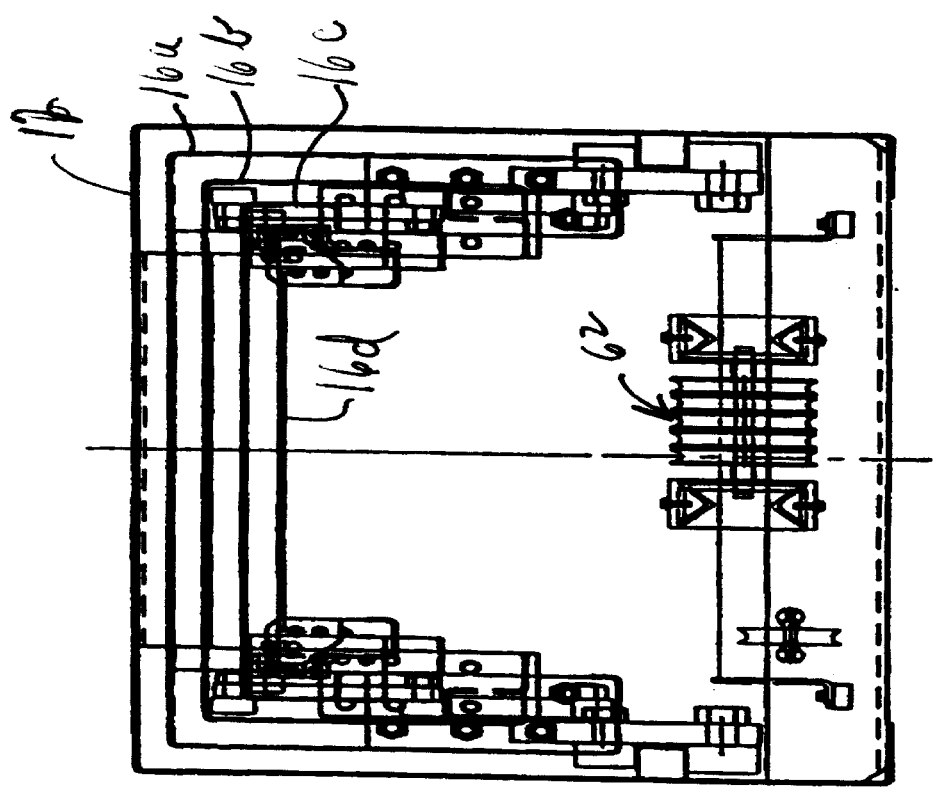
FIG. 6 is an end elevation taken from the lines VI—VI in FIG. 3.

Referring now specifically to the drawings, and the illustrative embodiments depicted therein, an extendable conveyor 10 includes a support structure, such as a support, or base unit, 12 and a mechanically extendable section 14 which is supported in a cantilevered fashion by base unit 12 (FIGS. 1–8). It should be understood that the invention may also be used with an extendable conveyor in which the mechanically extendable section is not supported in a cantilevered fashion. Mechanically extendable section 14 is made up of one or more subsections, or booms, 16a–16d. In a fully extended position, innermost section 16a is supported in a cantilevered fashion from base unit 12, and each successive subsection is supported in a cantilevered fashion from the next inner subsection up to subsection 16d, which is an outermost subsection. It should be understood that although the invention is illustrated with four extendable subsections, a greater or lesser number of subsections may be utilized. Also, a user interface section (not shown) may be supported at an end portion of mechanically extendable section 14 as illustrated in commonly assigned U.S. Pat. Nos. 6,006,893; 6,484,862; and 6,533,096, the disclosures of which are hereby incorporated herein by reference.

Figure 27:
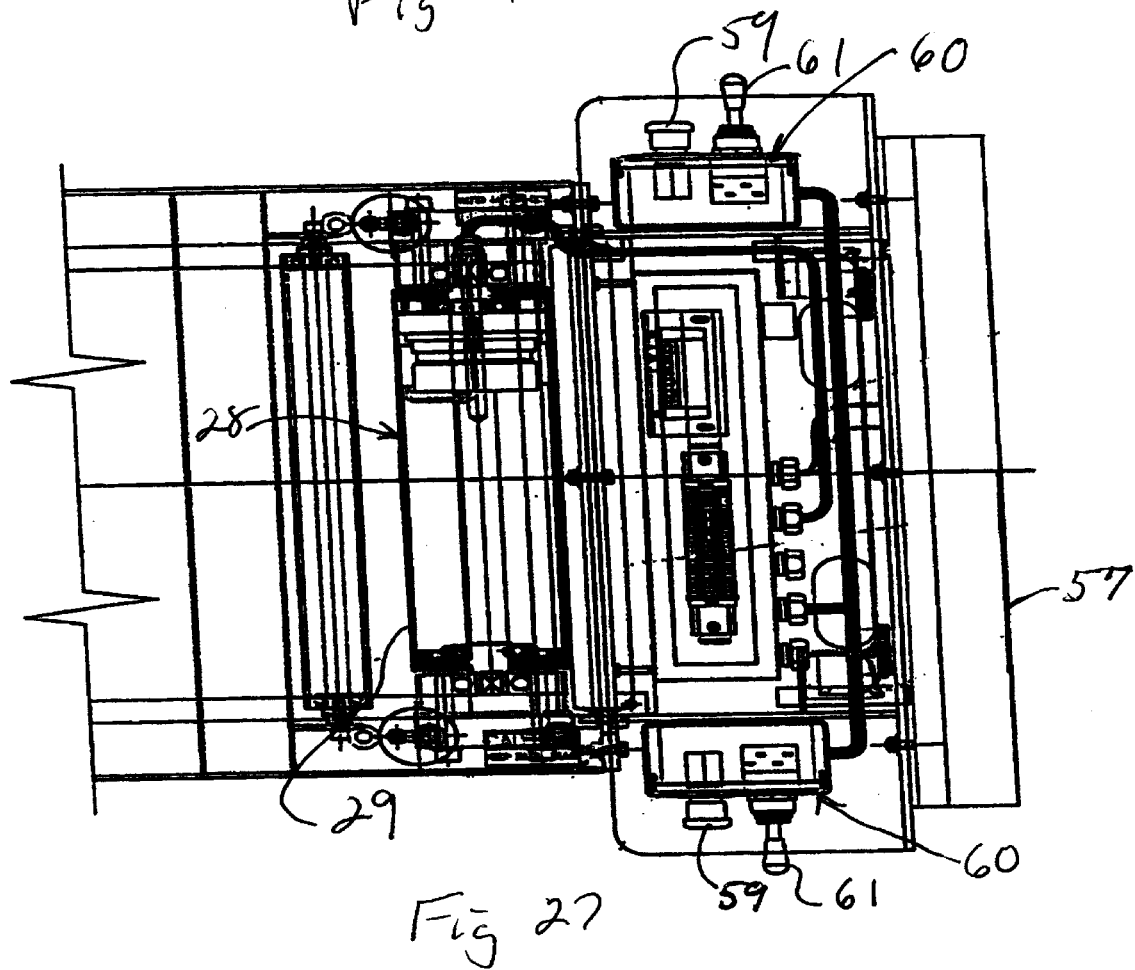
FIG. 27 is a top plan view of an outer end portion of the fourth boom.
Figure 28:
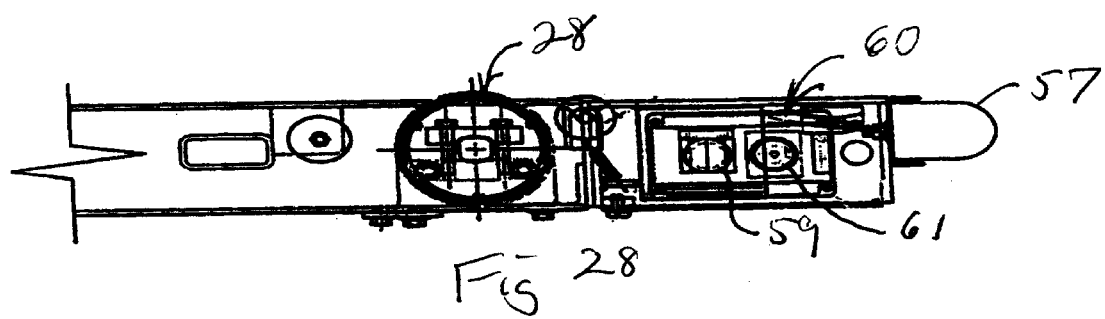
FIG. 28 is a side elevation of the end portion in FIG. 27.
Figure 29A:
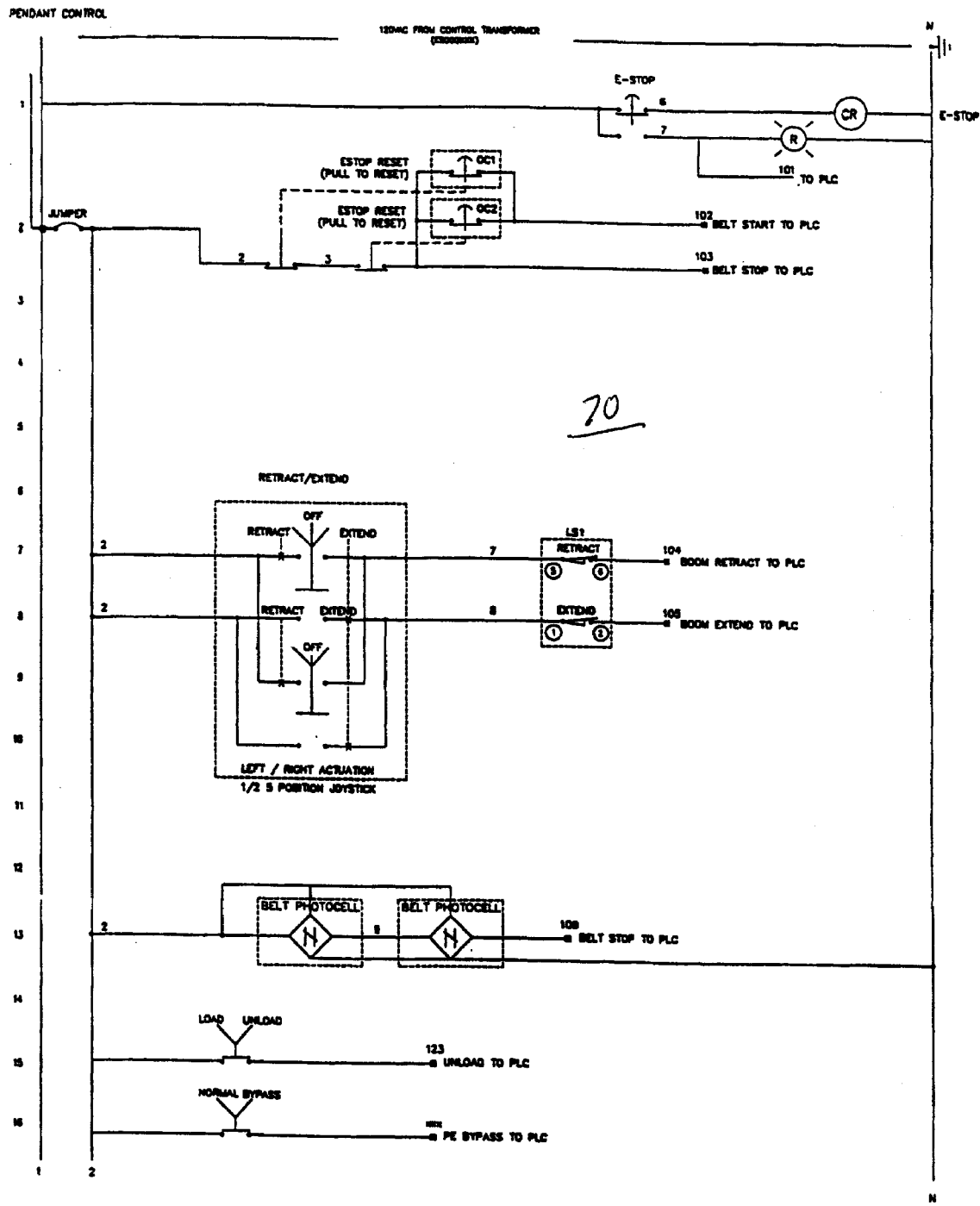
FIGS. 29a–29d are a ladder diagram of a control.
Figure 29B:
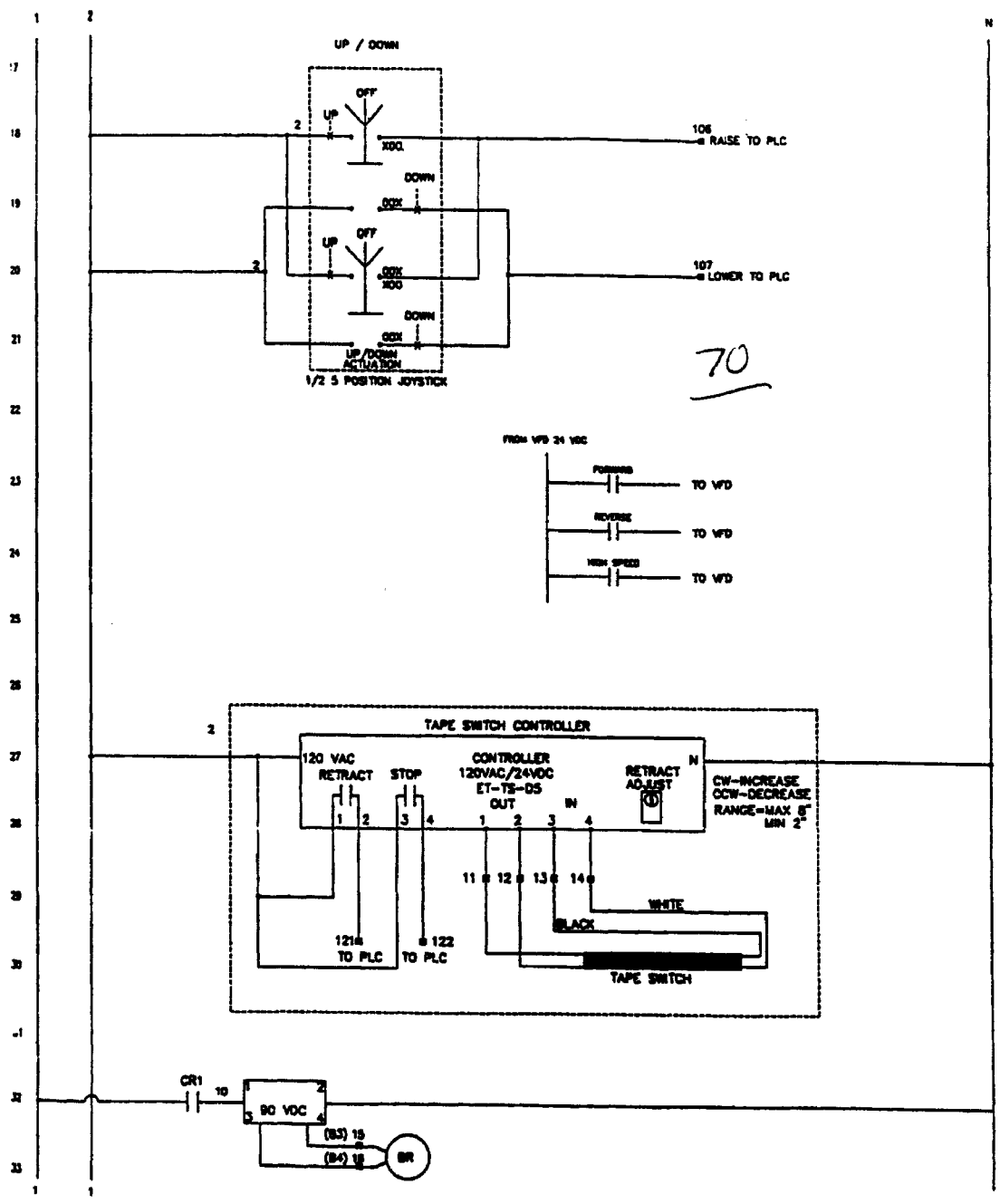
Figure 29C:
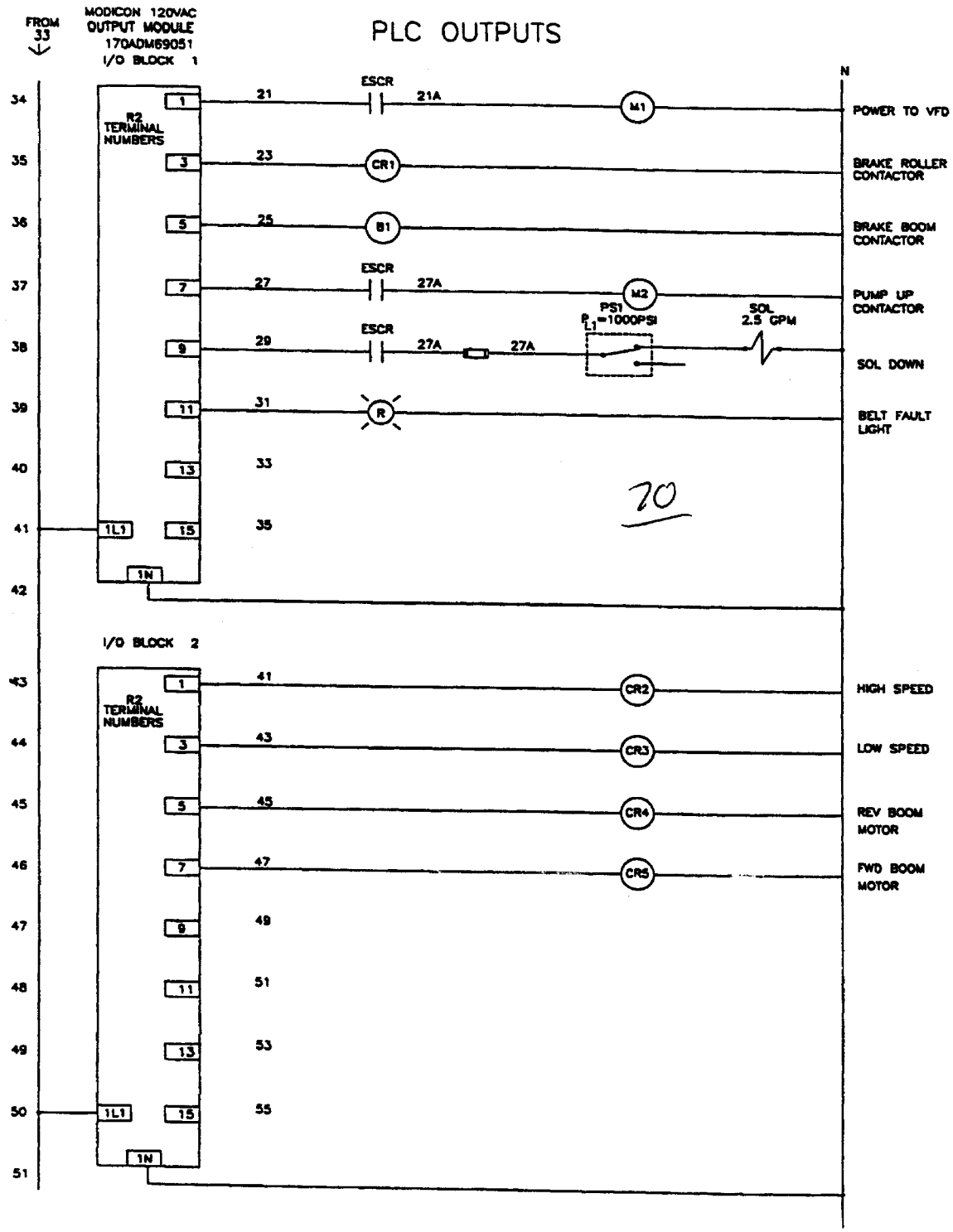
Figure 29D:
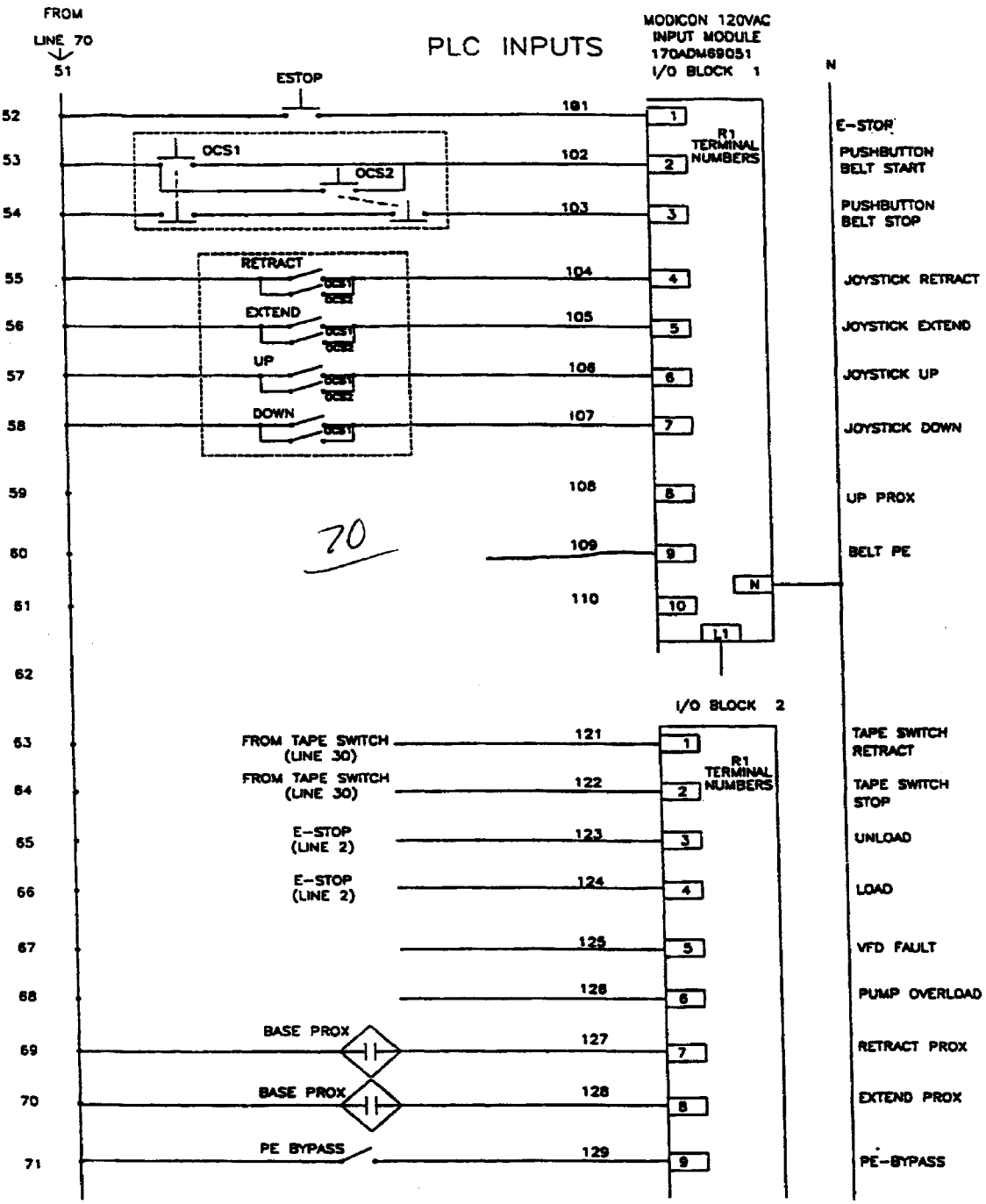

A continuous conveyor belt 18 is reeved among the base unit and the booms of the mechanically extendable section in order to define a conveying surface 19 supported by a belt support surface 20 defined by the uppermost portions of the booms 16a–16d and base unit 12, as illustrated in FIG. 4. Belt 18 is driven primarily by a drive unit 22 and provided under proper tension by a take-up device 24 as is generally known in the art. Extendable conveyor 10 includes a control 58 for controlling drive unit 22 and end pulley 28. Control 58 receives inputs from an operator panel 60 located at an outer end of outermost boom 16d. Operator panel 60 includes an input device 61, such as a joystick, or the like, which provides an operator the ability to extend and retract the extendable section 16 as well as to lower and raise the end of extendable section 16, such as by controlling one or more mounts 52 for the base unit. Mounts 52 may be hydraulic cylinders, electrically driven screws, or the like. As can be seen by reference to FIG. 27, control panel 60 may be duplicated on opposite lateral sides of boom 16d in order to allow control from either lateral side thereof. Control 58 may additionally receive inputs from an emergency stop (E-stop) switch 59 on operator panel 60 and/or from a stop bar 57 at an outermost end portion of outermost boom section 16d. E-stop button 59 allows the operator to stop all activity of the extendable conveyor and stop bar 57 shuts down the extension of the extendable conveyor should it encounter a stationary object. Control 58 may be embodied in a commercially available programmable logic controller, programmed with a ladder diagram 70 (FIGS. 29a–29d). Alternatively, control 58 can be embodied in hard-wired relay logic, dedicated computer-based controllers, or the like.

Mechanically extendable section 14 is extendable by driving conveyor belt 18 outwardly and retractable by driving the conveyor belt inwardly in combination with an electromechanical actuator for impeding belt 18 with respect to mechanically extendable section 14 when actuated. The electromagnetic actuator may be a brake device incorporated in an end pulley 28 of outermost subsection 16*d*. Alternatively, the electromagnetic actuator may be an electromechanical clamp, which substantially clamps the belt with respect to the mechanically extendable section, such as an external grasping member, or the like. In the illustrative embodiment, electromagnetic actuator 26 may be an electric brake, which may act through a gear set between a shaft of end pulley 28 and a rotating outer cylinder, or drum 29, of pulley 28 to impede rotation of the cylinder when actuated.

Extendable section 14 may be extended as follows. The drive belt 18 is stopped and control 58 causes the electromagnetic actuator to be actuated. This may be accomplished by the operator operating input device 61. This impedes movement of the belt with respect to the mechanical extendable section. The belt is driven with the uppermost surface driving outwardly which extends the extendable section outwardly. Once the extendable section is extended to the desired extend, control 58 deactuates the actuator and drive unit 22 propel belt 18 in either direction. This causes the conveyor to operate conveying surface 19 to convey articles into or out of the trailer. In order to retract the extendable section, the belt is stopped and the electromagnetic actuator is actuated. The belt is driven in a reverse direction by drive unit 22 with the uppermost surface driven toward base unit 12. This retracts the extendable section to the desired amount of extension. The electromagnetic actuator is then deactuated and the drive unit is operated to drive the belt in the desired direction. The ability to advance and retract the extendable section without the need of separate chains allows a lower guard 49 to be placed over each subsection 16*a*–16*d*. This enhances operator safety.

In yet another alternative embodiment, the electromagnetic actuator may be a motorized end pulley 28. Such a motorized pulley, which is known in the art, includes an electrical motor which drives the outer cylinder or drum 29 of the pulley through a speed reduction gear set. The electric motor and gear set may be either internal or external with respect to the outer cylinder. When used in extendable conveyor 10, such a motorized pulley operates as follows. In order to extend the extendable section, control 58 rotates the cylinder of the motorized pulley at a speed that is less than the speed that drive unit 22 is driving conveyor belt 18. This relative motion between drive unit 22 and pulley 28 causes extension or retraction of extendable section 16. In one embodiment, an electromagnetic brake is provided with the motorized pulley 28. Such a brake, which may operate on an output of the motor, brings rotation of cylinder 29 to a halt when electrical energy is removed from motorized pulley 28. Thus, with a brake associated with motorized pulley 28, the speed of the motorized pulley is zero in order to extend extendable section 16. The same occurs in order to retract the extendable section, except the control is operating the drive unit in the opposite direction to move the upper portion of the belt towards the base unit 12. Once the operator releases the input device, control 58 controls both the drive unit 22 and the motorized end pulley 28 at a common speed. Because both the drive unit and the motorized end pulley can be driven in either direction, they may be operated in this fashion to drive the conveyor belt outwardly in order to load articles to the truck or inwardly in order to unload articles from the truck. Because the drive unit and the motorized end pulley are operated in synchronism at generally the same speed to conveyor articles, the extendable section is maintained in a partially extended position. This may be accomplished without the requirement for friction devices. The use of a motorized end pulley allows the motor internal to the cylinder thereof to overcome any friction of its speed reducer thereby relieving the drive unit 22 of performing that additional function.

In the illustrative embodiment, drive unit 22 is a 2 HP motor capable of operation up to 80 feet per minute. Motorized end pulley 28 is a ½ HP motor capable of operation at 80 feet per minute. Such a motorized pulley is commercially available from Vander Graaf Corporation.

Other embodiments of the invention may be apparent to those skilled in the art. For example, rather than utilizing a brake in the motorized pulley, the motorized pulley could be operated at a different non-zero speed from the drive unit in order to incrementally extend or retract the extendable section 16. By way of example, if the motorized pulley is operated at a lesser speed than the drive unit while the conveying portion of the conveyor belt is being driven outwardly, the extendable section may be extended. Likewise, if the motorized pulley is operated at a lower speed than the drive unit while the conveying portion of the conveying belt is driven toward the base unit, the extendable section may be retracted. Other modifications may suggest themselves to those skilled in the art.

If needed to ensure that mechanically extendable section 14 only extends or retracts when electromagnetic actuator 26 is actuated, an optional friction device 30 may be provided at the interface between one or more subsections 16*a*–16*d* and between extendable section 14 and support 12. Friction device 30 may be stationary and provide an amount of friction, which may be overcome by drive unit 22 propelling belt 18. Alternatively, friction device 30 may be removable, retractable, or thereby being capable of providing even additional friction between a subsection and another subsection or the base unit. In the illustrative embodiment, friction device 30 may be a surface defined by a polymeric member which engages a sidewall 32*a*–32*d* of the adjacent subsection. In the illustrative embodiment, friction device 30 may apply a friction force in the range of between 20 to 100 pounds of resistance to the extension or retraction of the mechanically extendable section. It should be understood that friction device 30 is optional and may not be required in all applications.

Figure 9:
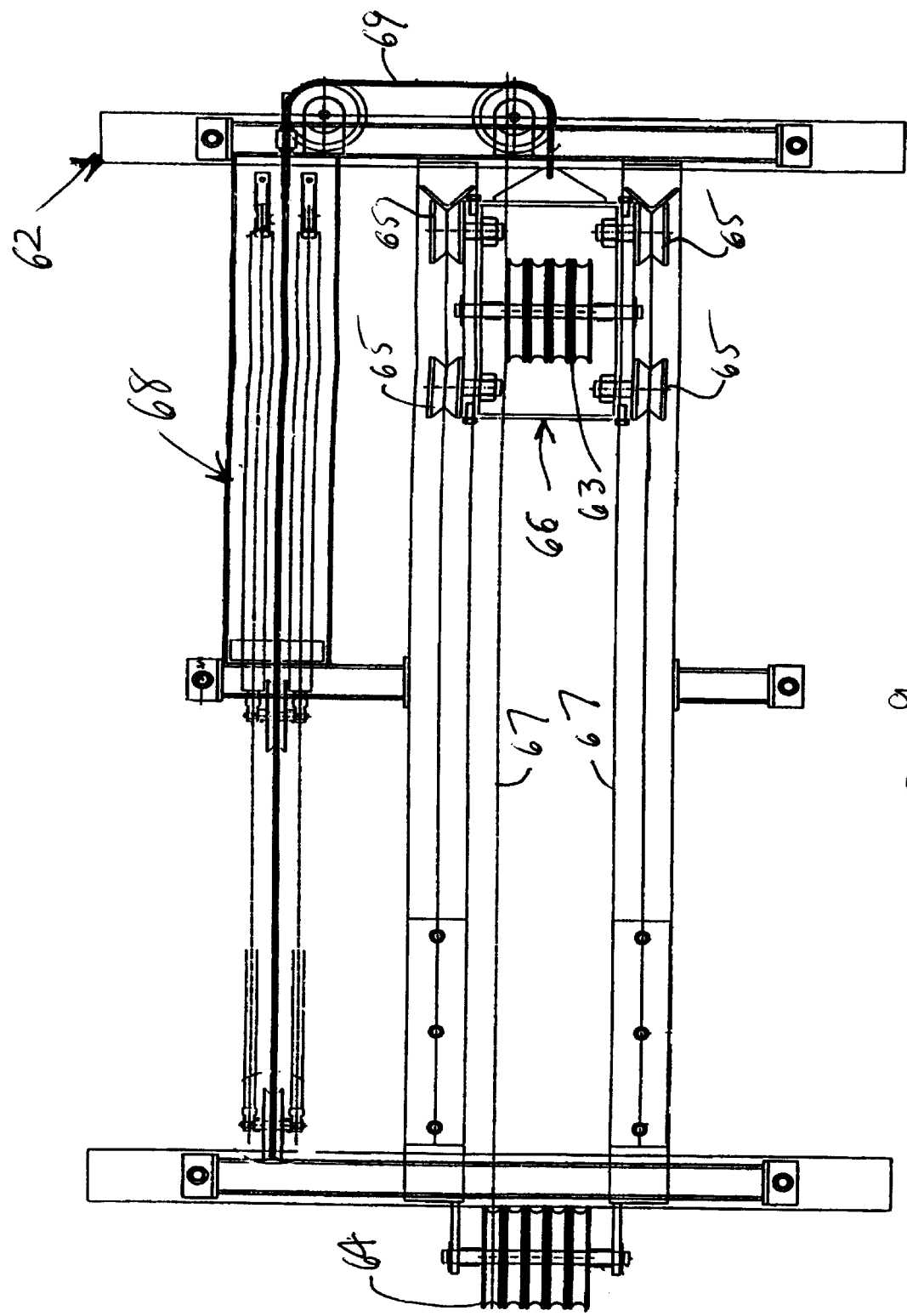
FIG. 9 is a top plan view of an electrical cable take-up.
Figure 23:
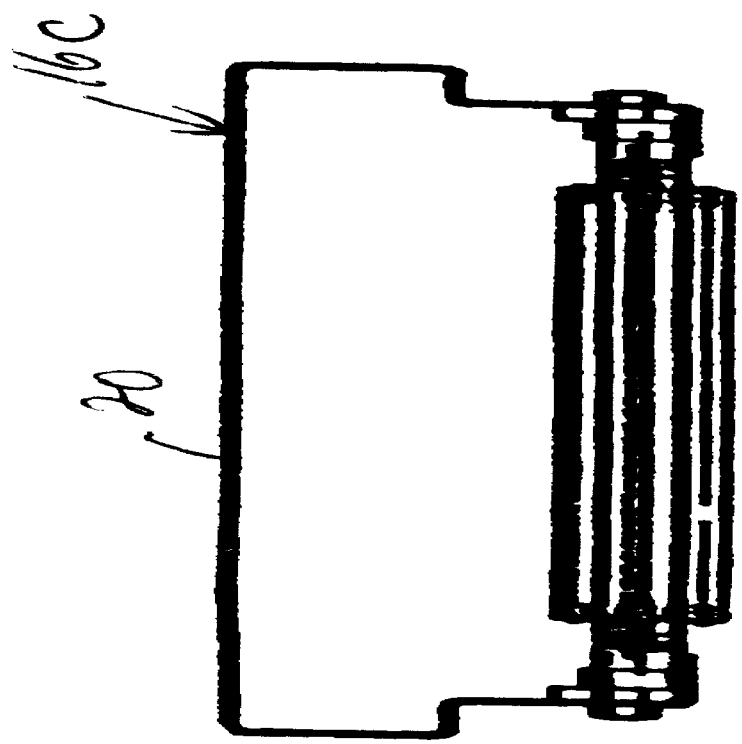
FIG. 23 is an end elevation taken from the direction XXIII—XXIII in FIG. 21.
Figure 22:
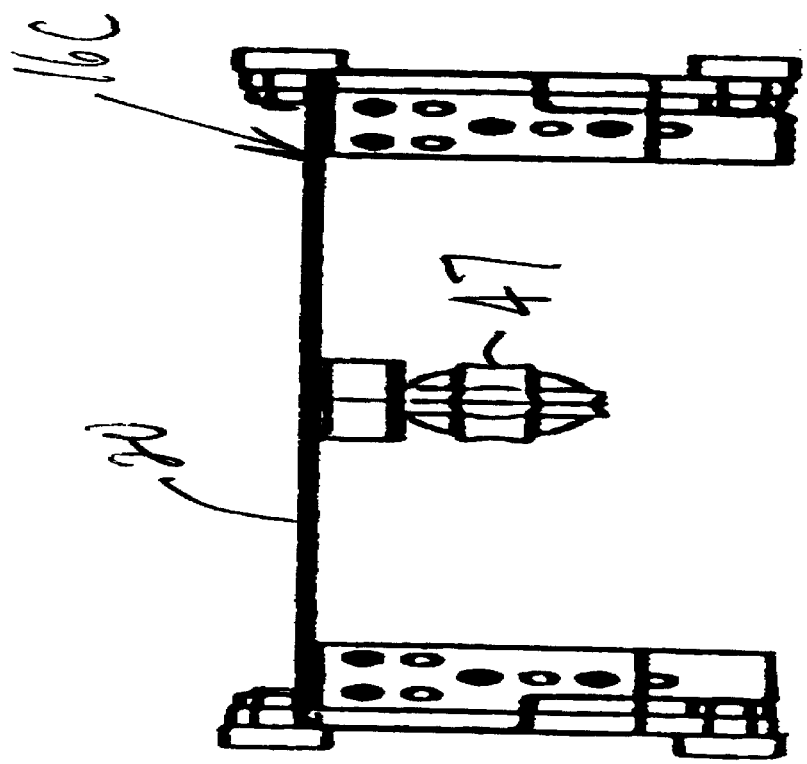
FIG. 22 is an end elevation taken from the direction XXII—XXII in FIG. 21.
Figure 26:
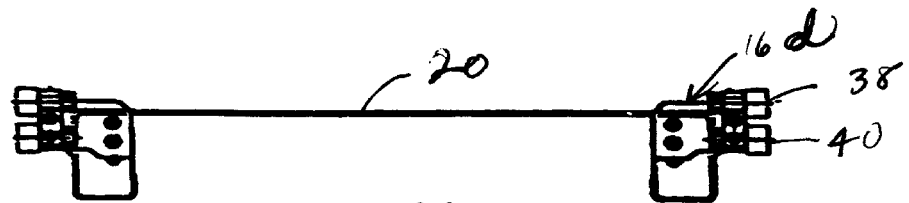
FIG. 26 is an end elevation taken from the direction XXVI—XXVI in FIG. 25.

A cable (not shown) extends generally continuously from control 58 to operator panel 60 and end pulley 28. In order to accommodate slack in the cable as the extendable section 16 retracts, a cable take-up 62 is provided (FIG. 9). Cable take-up 62 includes a stationary sheave assembly 64, containing one or more sheaves and a movable sheave assembly 66 containing one or more moveable sheaves 63. Moveable sheave assembly 66 includes a plurality of grooved wheels 65 which freely move along a set of rails 67. A biasing device 68, such as one or more gas springs, is interconnected with moveable sheave assembly 66, such as by a cable 69.

The electrical cable (not shown) is reeved around sheaves 63 and 64 multiple times and is then reeved throughout the booms 16*a*–16*d* to the end pulley 28 and the operator panel 60. The electrical cable is guided by a cable guide roller 47 at a rear portion at each of the booms. In operation, as the electrical cable is paid out as the extendable section is extended, moveable sheave assembly 66 is drawn towards stationary sheave assembly 64 which biases biasing device 68. As the extendable section is retracted, the slack created in the electrical cable allows biasing device 68 to pull moveable sheave assembly 66 away from stationary sheave assembly 64 thereby taking up the slack in the electrical cable. An advantage of cable take-up 62 is that it accommodates non-coordinated movement of the extendable sections, or booms, 16a–16d. This is accommodated in a manner that does not require any slip rings as is conventional in prior cable take-up devices. This enhances the reliability of the control system.

One or more subsections 16a–16d may each be made from a single sheet of metal which is formed, such as using a press-brake, in a manner which defines a portion of belt support surface 20 and corresponding side members 32a–32d on the respective booms. By forming one or more of the booms substantially of a unitary sheet of metal, the extendable conveyor may be made lighter in weight. In addition, the necessity for welding is eliminated or, at least, significantly reduced. As best illustrated in FIG. 4, a pair of horizontal tracks 42, 51 may be formed in respective side members 32c, 32b of respective booms 16c, 16b in order to provide cantilevered support for adjacent booms. While the base unit 10 may also lend itself to manufacture from a single sheet of metal, at least one side bracket 34 may be welded to side 32e of base member 12 in order to provide cantilevered support for mechanically extendable section 14. Moreover, some of the booms may be made by two or more sheets of metal joined by a reinforcing plate as illustrated by top plate 32f in FIG. 15.

A cantilevered support 36 is provided at an inner end portion of outer subsection 16d which is fully mounted to the outer subsection and which does not change irrespective of the position of subsection 16d with respect to subsection 16c. Cantilever support 36 is provided by one or more upper rollers 38 at an innermost portion of subsection 16d and at least one lower roller 40 spaced outwardly of roller 38. With rollers 38 and 40 mounted to subsection 16d, they provide generally constant support for section 16d irrespective of the position of section 16d with respect to the next innermost section 16c. Roller 38 engages a lower surface of support surface 20 of subsection 16c. Lower rollers 40 engage a track 42 formed in sidewall 32c. The next most inward support section 16c includes a support assembly 46 at an innermost portion of subsection 16c and at least one support roller 48 mounted at a forward portion of the next most inward subsection 16b. Support assembly 46 includes a pair of upper and lower rollers 50, the upper one of which operates against an upper surface of subsection 16b, which is defined below support surface 20. The lowermost support roller 50 operating in a track 51 formed in sidewall 32b of subsection 16b. The remaining subsections are supported generally in the manner disclosed in the '809 patent.

As with the '809 patent, the innermost portion of the support for one or more subsections 16a–16d may be vertically adjustable. With the innermost portion of each subsection adjusted upwardly, the conveying surface defined by belt 18 may be bowed whereby, with the extendable unit extended, a central portion 56 thereof may be vertically higher than an imaginary straight line L interconnecting pulley 28 and an upper end portion 54 of base unit 12. This allows end portion 54 to be lower than a central portion 56 while allowing the unit to fit within the truck. One or both mounts 52 may be vertically adjustable as illustrated in the '809 patent in order to allow the inner portion of the conveying surface to slope upwardly toward the trailer.

This particular arrangement of the extendable conveyor 10 is especially useful where the extendable conveyor is positioned at a surface that is generally of the same elevation to the surface which supports the trailer, as illustrated in FIG. 1. This allows the base unit 12 to be generally at or below the level of the floor of the truck while allowing the extendable section 16 to clear the truck door opening without raising the outermost end portion of the extendable section too high above the floor of the truck. This allows any conveyor connected with end portion 54 to be closer to floor level and also allows any operator station at base unit 12 to be able to stand at/or near the floor. Moreover, the positioning of the outer end portion of the extendable section closer to the floor of the truck provides for ergonomic use of extendable conveyor 10.

It should be apparent to the skilled artisan that, while the various features of the invention are illustrated herein as being used together, these features may have individual application in the art. Changes and modifications in the specifically described embodiments can be carried out without departing from the principles of the invention which is intended to be limited only by the scope of the appended claims, as interpreted according to the principles of patent law including the doctrine of equivalents.

The invention claimed is:

1. An extendable conveyor, comprising:
   a support structure;
   an extendable section made up of a plurality of booms, said booms being extendable between a fully retracted position and a fully extended position, said extendable section supported in a cantilever fashion by said support structure;
   a conveyor belt reeved among said booms thereby defining a conveying surface;
   a drive operable to reversibly drive said conveyor belt in opposite directions;
   an electromechanical actuator that is operative to impede movement of said belt with respect to said extendable section; and
   a control, being operable to partially extend said extendable section by controlling said drive to operate said conveyor belt in one direction while controlling said electromechanical actuator to impede movement of the conveyor belt with respect to the extendable section, said control being operable to partially retract said extendable section by controlling said drive to operate said conveyor belt in an opposite direction while controlling said electromechanical actuator to impede movement of said conveyor belt with respect to said extendable section;
   wherein said conveyor belt being operable to convey articles by said control controlling said drive to operate said conveyor belt in one of said directions while controlling said electromechanical actuator to not substantially impede movement of said conveyor belt with respect to said extendable section;
   wherein said electromechanical actuator is incorporated within an end pulley at an outermost one of said at least one boom.

2. The extendable conveyor of claim 1 including an operator panel at an outer end portion of said extendable section, said panel including an operator input device to selectively cause said control to at least partially extend said extendable section or to at least partially retract said extendable section.

3. The extendable conveyor of claim 2 including an electrical cable, said electrical cable extending from said control to said operator panel and said electromechanical actuator.

4. The extendable conveyor of claim 3 including a cable take-up assembly at said support for taking-up slack in said electrical cable.

5. The extendable conveyor of claim 4 wherein said cable take-up assembly comprises at least one stationary sheave, at least one moveable sheave and a biasing device, said biasing device biasing said sheaves apart, wherein said cable is reeved around said sheaves.

6. The extendable conveyor of claim 5 wherein said at least one stationary sheave comprises a plurality of stationary sheaves and wherein said at least one moveable sheave comprises a plurality of moveable sheaves.

7. The extendable conveyor of claim 1 wherein said plurality of booms nest within each other when said extendable section is fully retracted.

8. The extendable conveyor of claim 1 wherein said extendable section being bowed when in an extended position wherein a central portion of said conveying surface is above an imaginary straight line extending between opposite end portions of said conveying surface.

9. The extendable conveyor of claim 1 including at least one friction device for providing friction at said extendable section to resist retraction or extension of said extendable section when said control is not actuating said electromechanical actuator.

10. The extendable conveyor of claim 1 wherein at least one of said booms is made substantially from a unitary sheet of metal, said unitary sheet of metal forming a three-dimensional shape, said three-dimensional shape defining a combination of a horizontal belt supporting surface and support sides extending from said belt supporting surface, said three-dimensional shape further defining a pair of horizontal flanges extending inwardly from said support sides and an opening between said flanges, said belt supporting surface supporting a portion of said conveyor belt at said conveying surface.

11. An extendable conveyor, comprising:
a support structure;
an extendable section made up of a plurality of booms, said booms being extendable between a fully retracted position and a fully extended position, said extendable section supported in a cantilever fashion by said support structure;
a conveyor belt reeved among said booms thereby defining a conveying surface;
a drive at said support structure;
a braking pulley at an outermost one of said at least one boom, said braking pulley comprising a cylinder and a cylinder brake, said cylinder brake being operable to apply a braking force to said cylinder when actuated;
a conveyor belt reeved among said drive and said braking pulley thereby defining a conveying surface;
a control, said control being operable to partially extend said extendable section by controlling said drive to operate said conveyor belt in one direction while actuating said braking pulley, said control being operable to partially retract said extendable section by controlling said drive to operate said conveyor belt in an opposite direction while actuating said braking pulley;
wherein said conveyor belt being operable to convey articles by said control controlling said drive to operate said conveyor belt in one of said directions while deactuating said braking pulley.

12. The extendable conveyor of claim 11 wherein said braking pulley comprises an idler pulley.

13. The extendable conveyor of claim 11 wherein said braking pulley comprises a motorized pulley.

14. The extendable conveyor of claim 13 wherein said motorized pulley comprises a cylinder, a drive motor within said cylinder a speed reducer between an output of said motor and said cylinder, and a cylinder brake.

15. The extendable conveyor of claim 11 including at least one friction device providing friction at said extendable section to resist retraction or extension of said extendable section when said control is not actuating said cylinder brake.

16. The extendable conveyor of claim 11 including an operator panel at an outer end portion of said extendable section, said panel including an operator input device for selectively causing said control to at least partially extend said extendable section or to at least partially retract said extendable section.

17. The extendable conveyor of claim 16 including an electrical cable, said electrical cable extending from said control to said operator panel and said braking pulley.

18. The extendable conveyor of claim 17 including a cable take-up assembly at said support for taking up slack in said electrical cable.

19. The extendable conveyor of claim 18 wherein said cable take-up assembly comprises at least one stationary sheave, at least one moveable sheave and a biasing device, said biasing device biasing said sheaves apart, wherein said cable is reeved around said sheaves.

20. The extendable conveyor of claim 19 wherein said at least one stationary sheave comprises a plurality of stationary sheaves and wherein said at least one moveable sheave comprises a plurality of moveable sheaves.

21. The extendable conveyor of claim 11 wherein at least one of said booms is made substantially from a unitary sheet of metal, said unitary sheet of metal forming a three-dimensional shape, said three-dimensional shape defining a combination of a horizontal belt supporting surface and support sides extending from said belt supporting surface, said three-dimensional shape further defining a pair of horizontal flanges extending inwardly from said support sides and an opening between said flanges, said belt supporting surface supporting a portion of said conveyor belt at said conveying surface.

* * * * *